(12) United States Patent
Tiwald

(10) Patent No.: US 6,801,312 B1
(45) Date of Patent: Oct. 5, 2004

(54) METHOD FOR EVALUATING COMPLEX REFRACTIVE INDICIES UTILIZING IR RANGE ELLIPSOMETRY

(75) Inventor: Thomas E. Tiwald, Lincoln, NE (US)

(73) Assignee: J.A. Woollam Co. Inc., Lincoln, NE (US)

( * ) Notice: Subject to any disclaimer, the term of this patent is extended or adjusted under 35 U.S.C. 154(b) by 475 days.

(21) Appl. No.: 09/888,598

(22) Filed: Jun. 25, 2001

Related U.S. Application Data

(63) Continuation-in-part of application No. 09/474,318, filed on Dec. 29, 1999.
(60) Provisional application No. 60/212,848, filed on Jun. 26, 2000.

(51) Int. Cl.⁷ .............................................. G01N 4/00
(52) U.S. Cl. ...................................................... 356/369
(58) Field of Search ................................ 356/364, 369

(56) References Cited

U.S. PATENT DOCUMENTS

| | | | |
|---|---|---|---|
| 4,053,232 A | 10/1977 | Dill et al. ................... | 356/118 |
| 4,668,086 A | 5/1987 | Redner ....................... | 356/367 |
| 4,905,170 A * | 2/1990 | Forouhi et al. .............. | 356/631 |
| 5,329,357 A | 7/1994 | Bernoux et al. ............. | 356/369 |
| 5,373,359 A | 12/1994 | Woollam et al. ............ | 356/328 |
| 5,504,582 A | 4/1996 | Johs et al. ................... | 356/369 |
| 5,521,706 A | 5/1996 | Green et al. ................. | 356/369 |
| 5,581,350 A | 12/1996 | Chen et al. .................. | 356/369 |
| 5,595,916 A * | 1/1997 | Fujimura et al. ........ | 250/341.4 |
| 5,596,406 A | 1/1997 | Rosencwaig et al. ....... | 356/327 |
| 5,666,201 A | 9/1997 | Johs et al. ................... | 356/369 |
| 5,757,494 A | 5/1998 | Green et al. ................. | 356/369 |
| 5,796,983 A | 8/1998 | Herzinger ................... | 395/500 |
| 5,805,285 A | 9/1998 | Johs et al. ................... | 356/369 |
| 5,835,222 A | 11/1998 | Herzinger ................... | 356/369 |
| 5,872,630 A | 2/1999 | Johs et al. ................... | 356/369 |

* cited by examiner

Primary Examiner—Zandra V. Smith
(74) Attorney, Agent, or Firm—James D. Welch

(57) ABSTRACT

A method of evaluating mathematical model parameters which describe directions and magnitudes of real and imaginary components of orthogonally related Kramers-Kroenig consistent dielectric functions or complex refractive indicies in an optically thick material system which presents with an optical axis oriented either in-plane or out-of-plane, with respect to an alignment surface of the optically thick material system. The method is particularly applicable to investigation of optically thick material systems which are uniaxial or biaxial using IR range wavelengths.

27 Claims, 22 Drawing Sheets

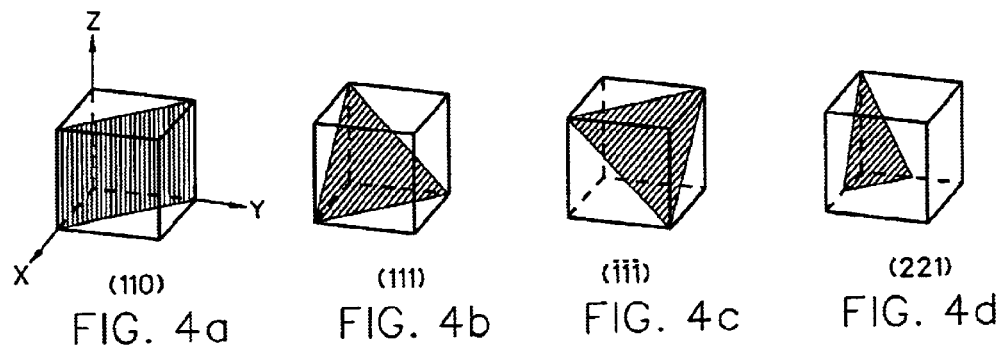
FIG. 4a (110)  FIG. 4b (111)  FIG. 4c (1̄1̄1̄)  FIG. 4d (221)
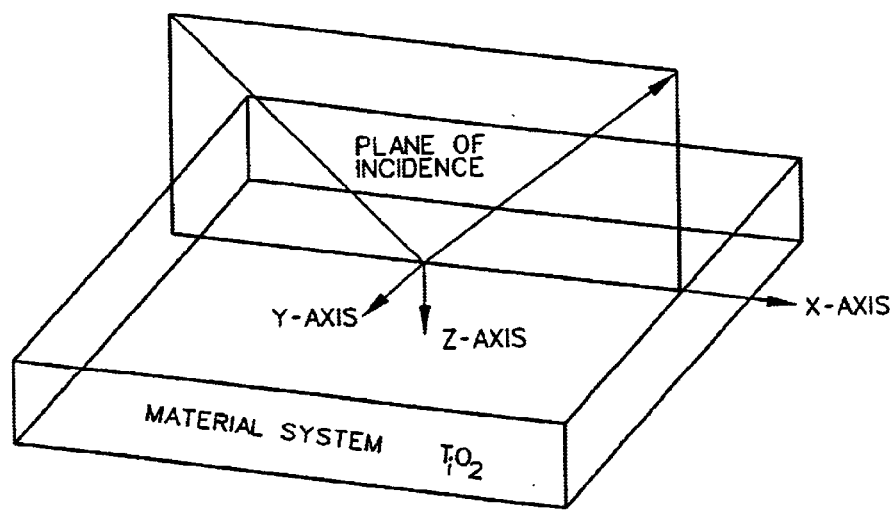
FIG. 5a

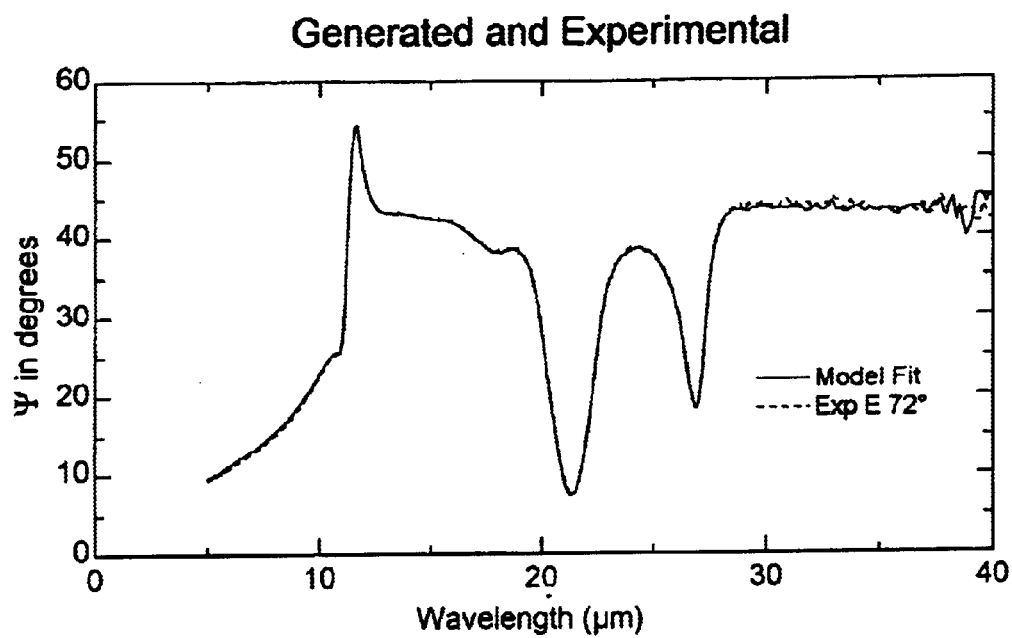
FIG. 6a1
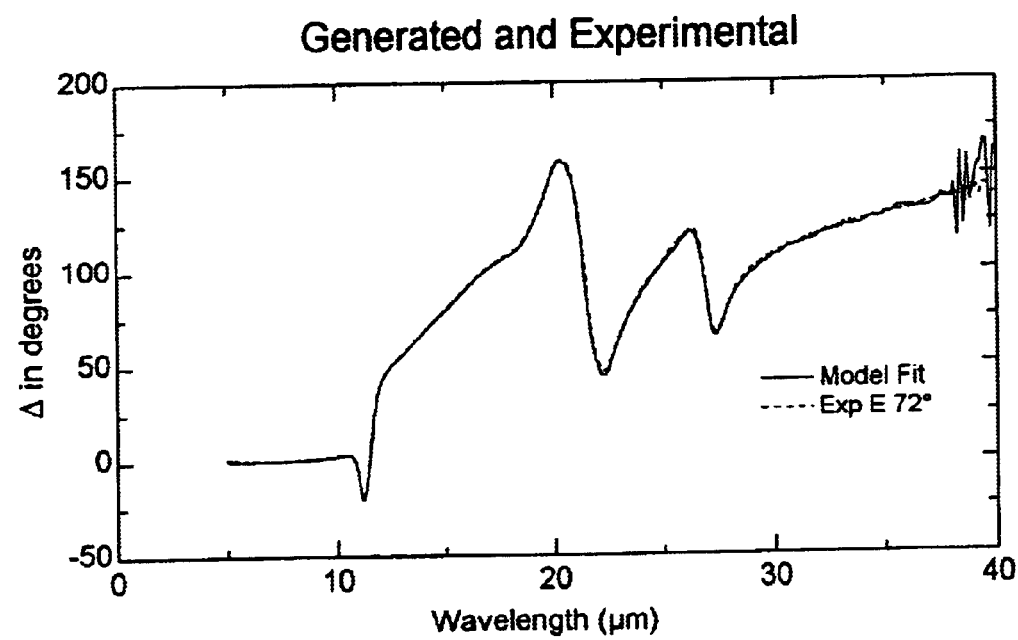
FIG. 6a2

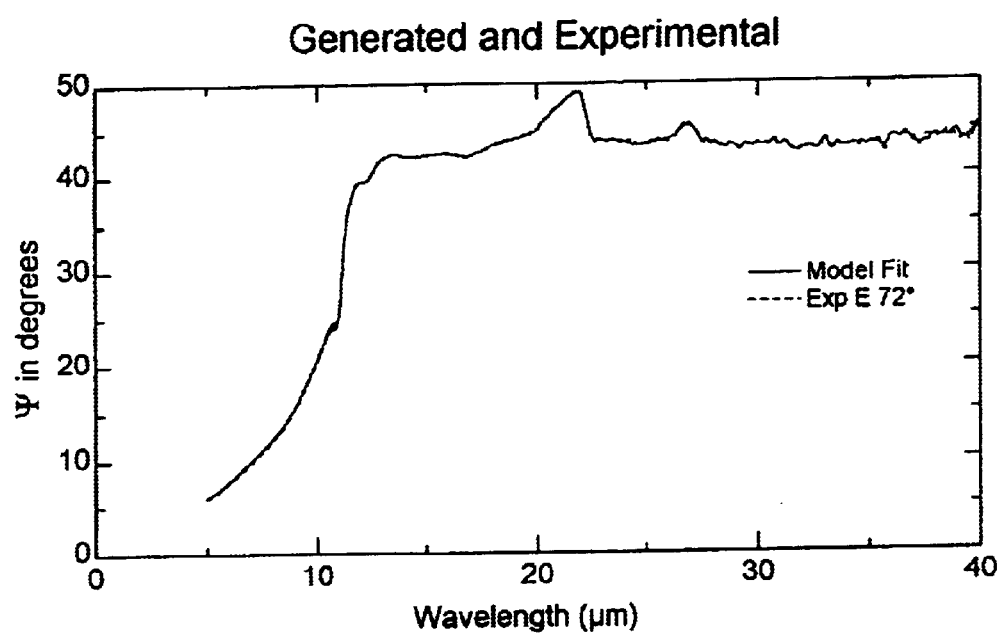
FIG. 6b1
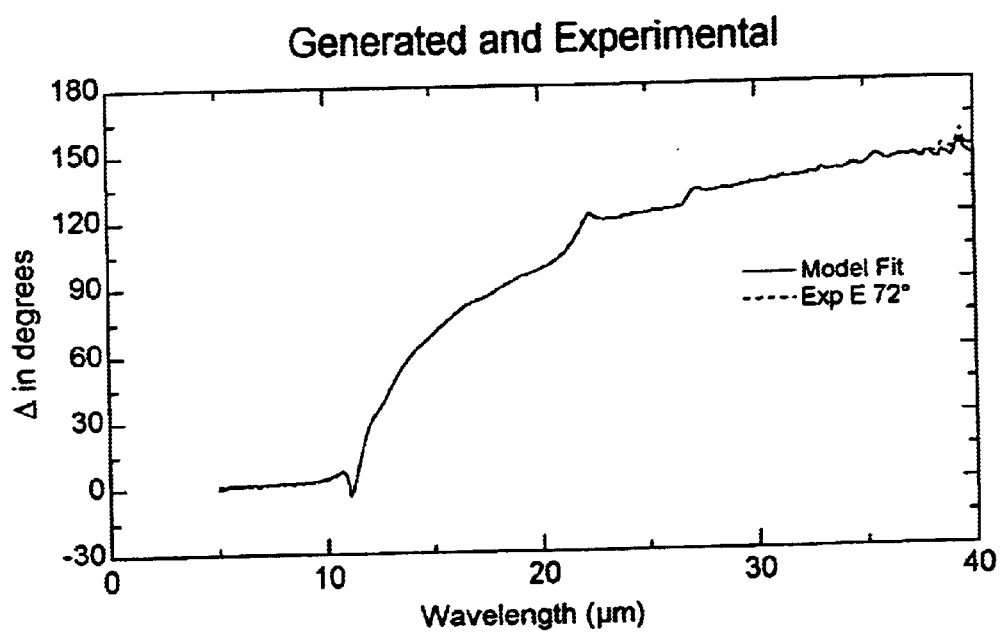
FIG. 6b2

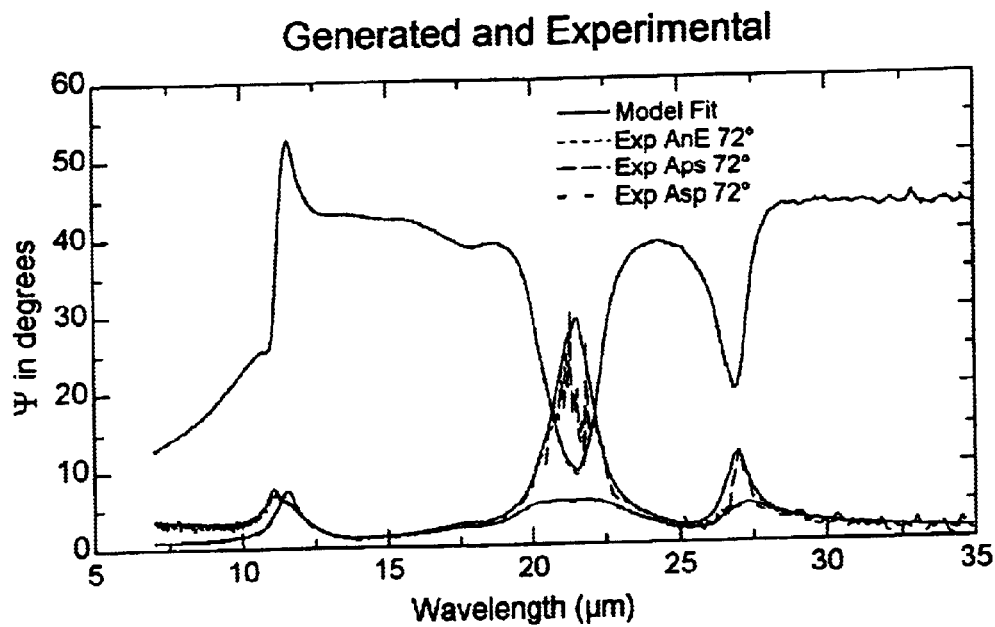
FIG. 6c1
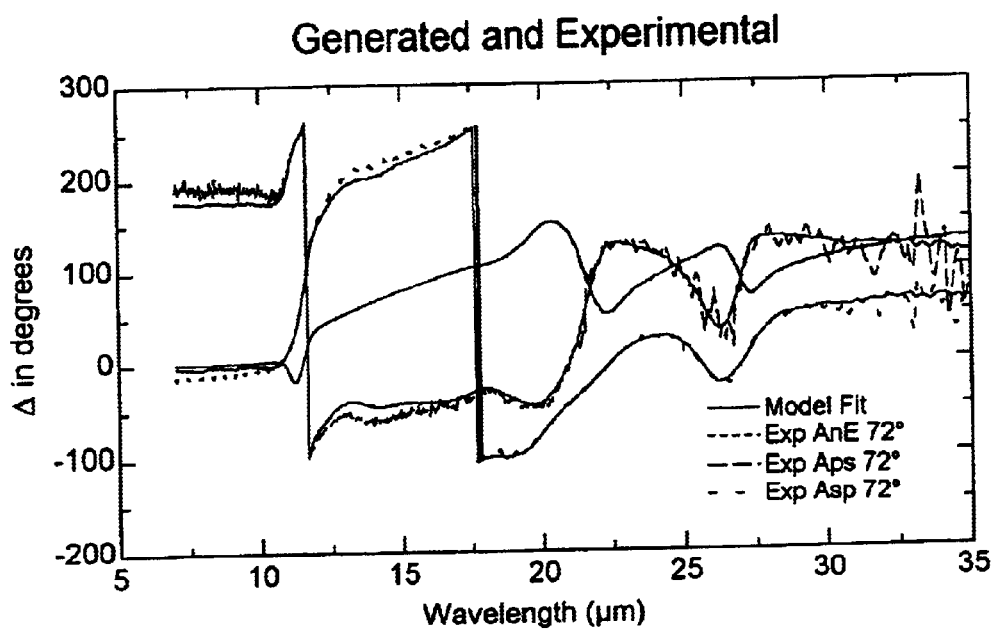
FIG. 6c2

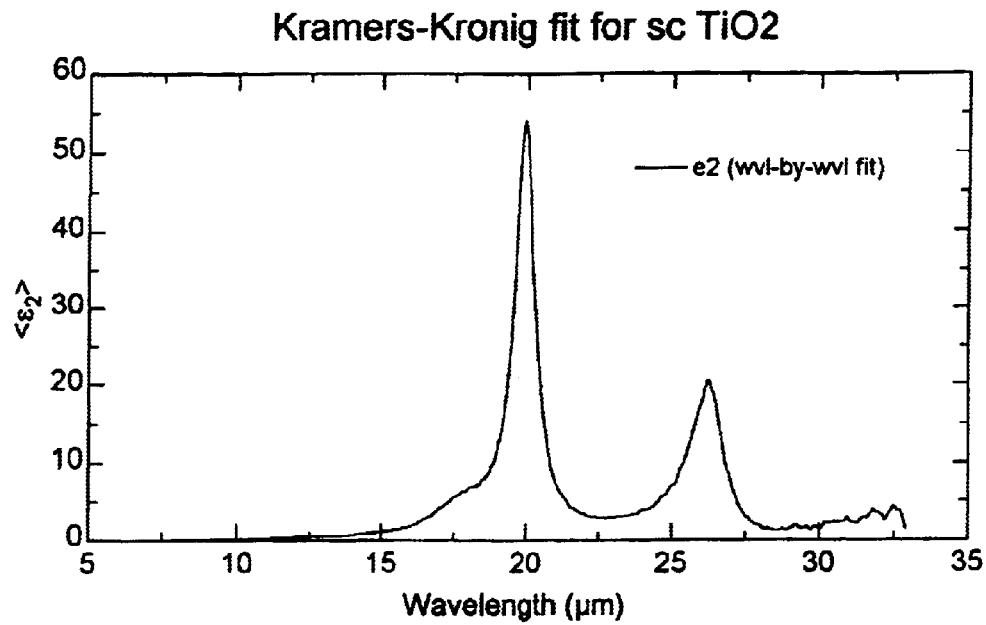
FIG. 6d1
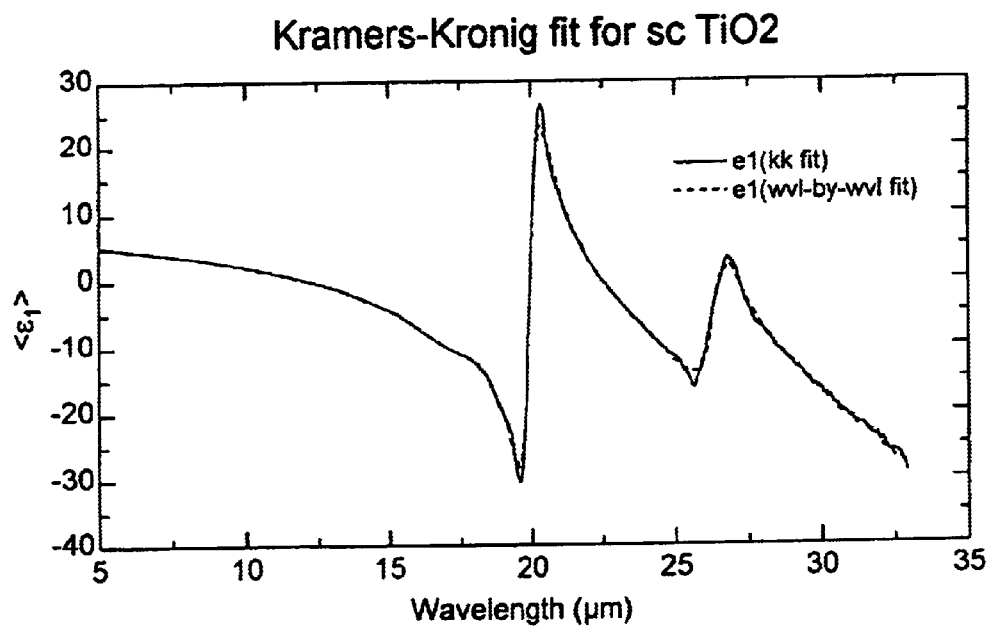
FIG. 6d2

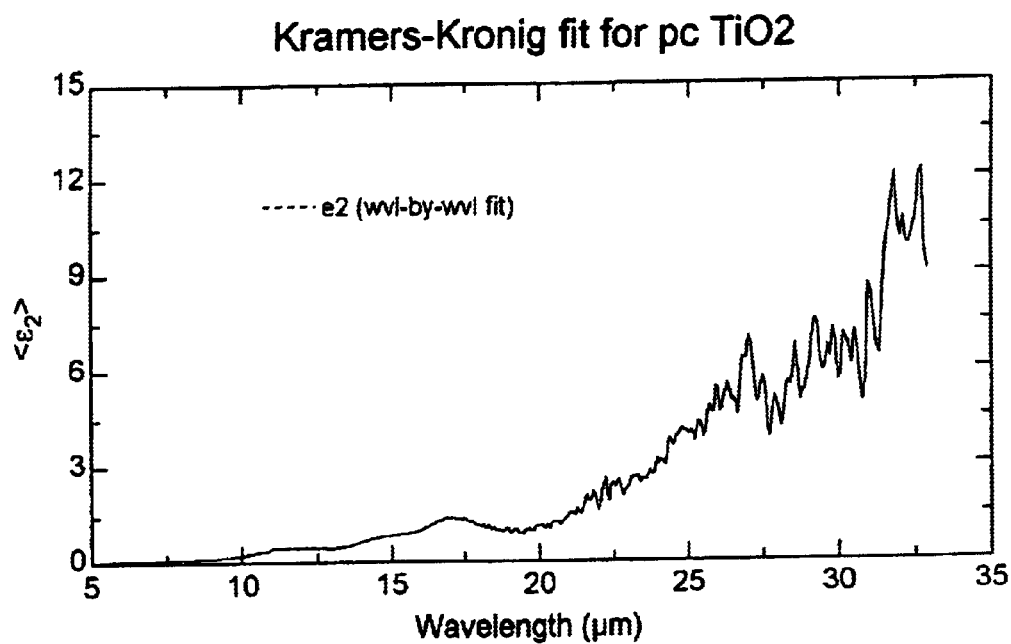
FIG. 6e1
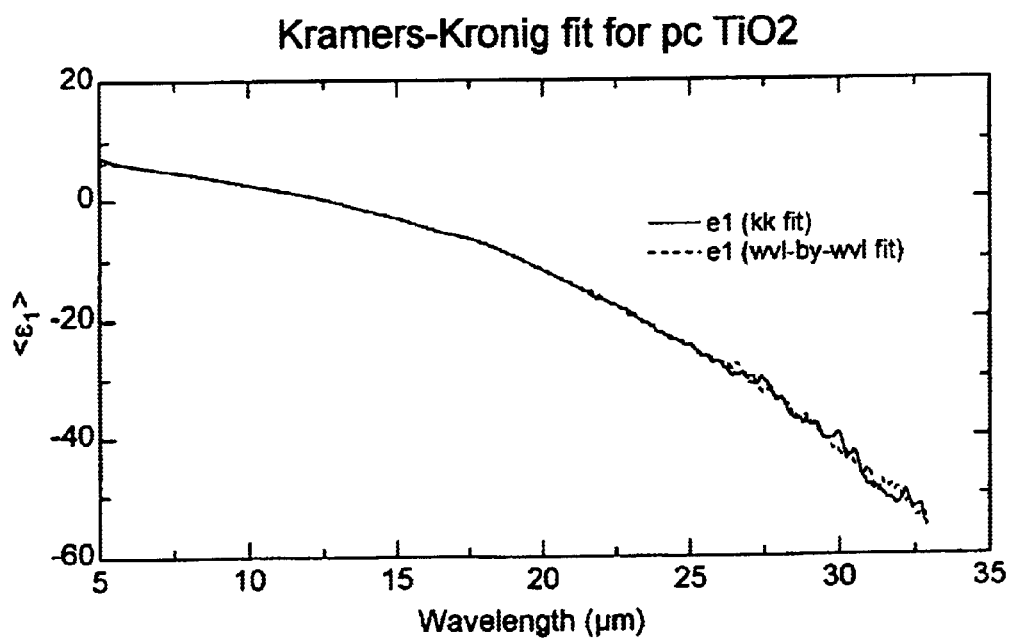
FIG. 6e2

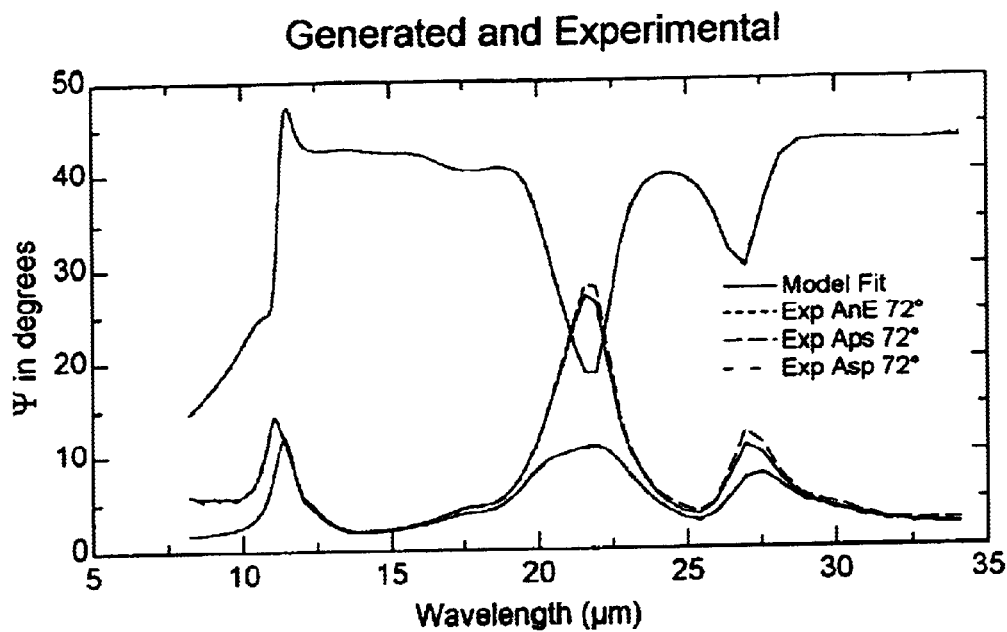
FIG 7a1
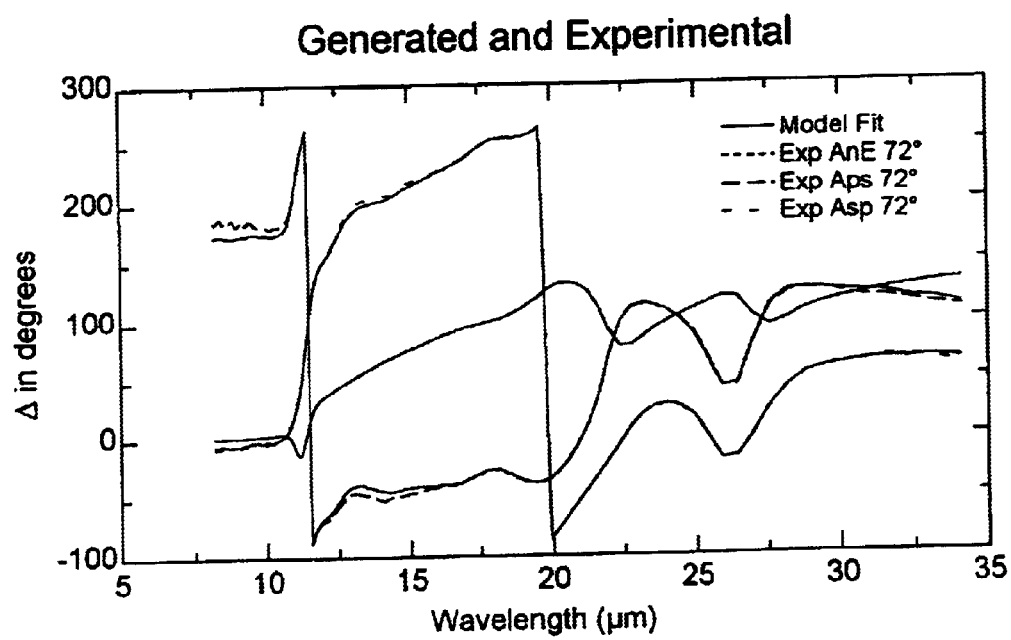
FIG. 7a2

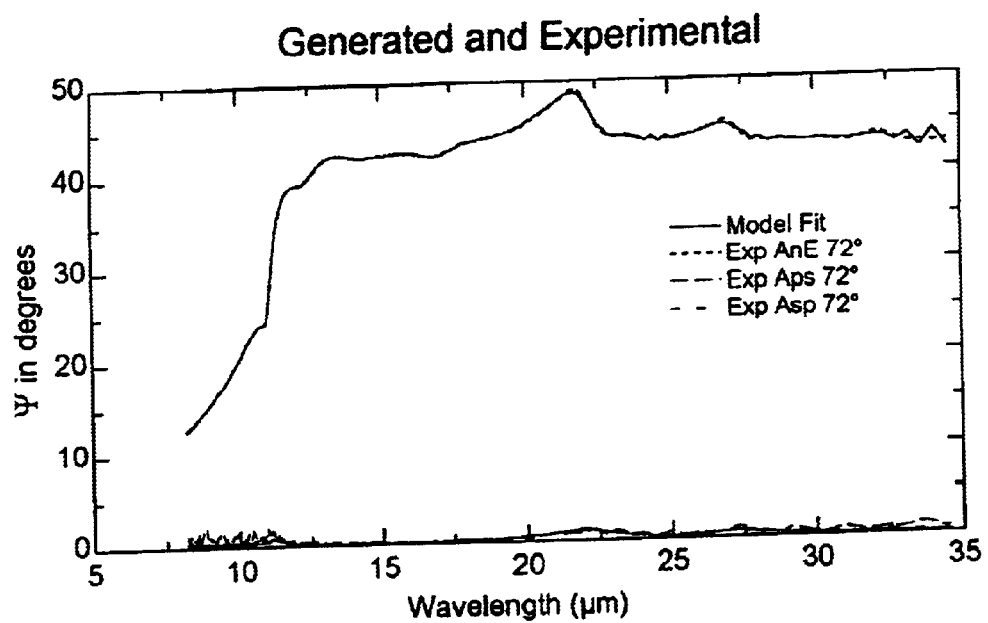
FIG. 7b1
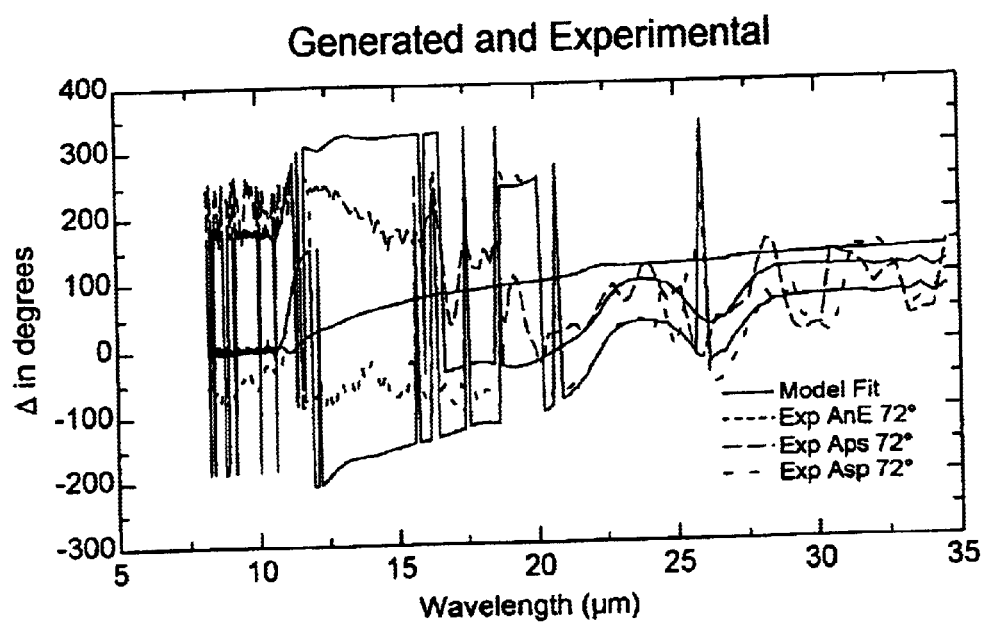
FIG. 7b2

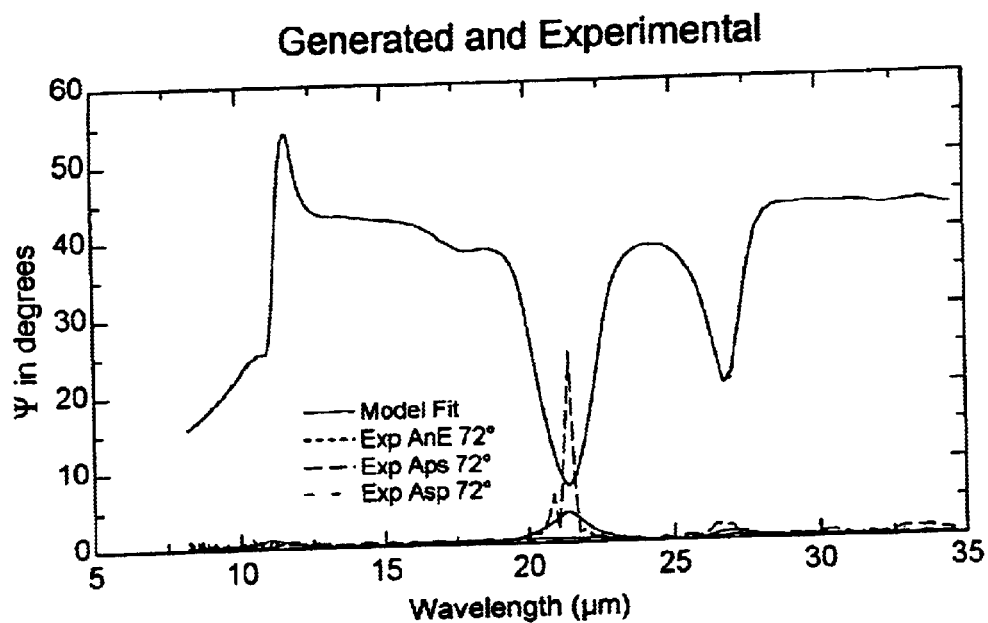
FIG. 7c1
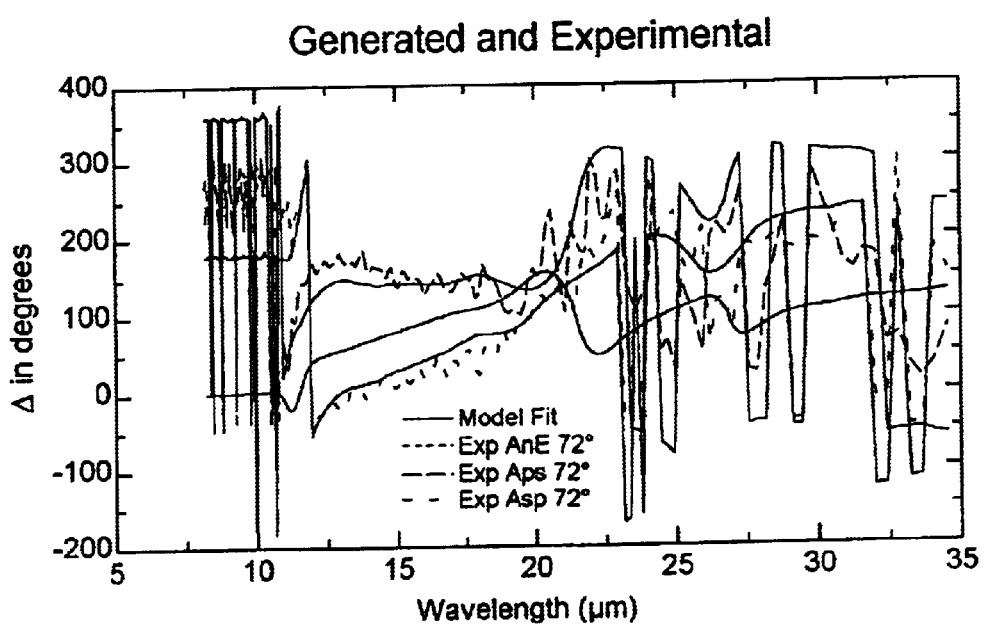
FIG. 7c2

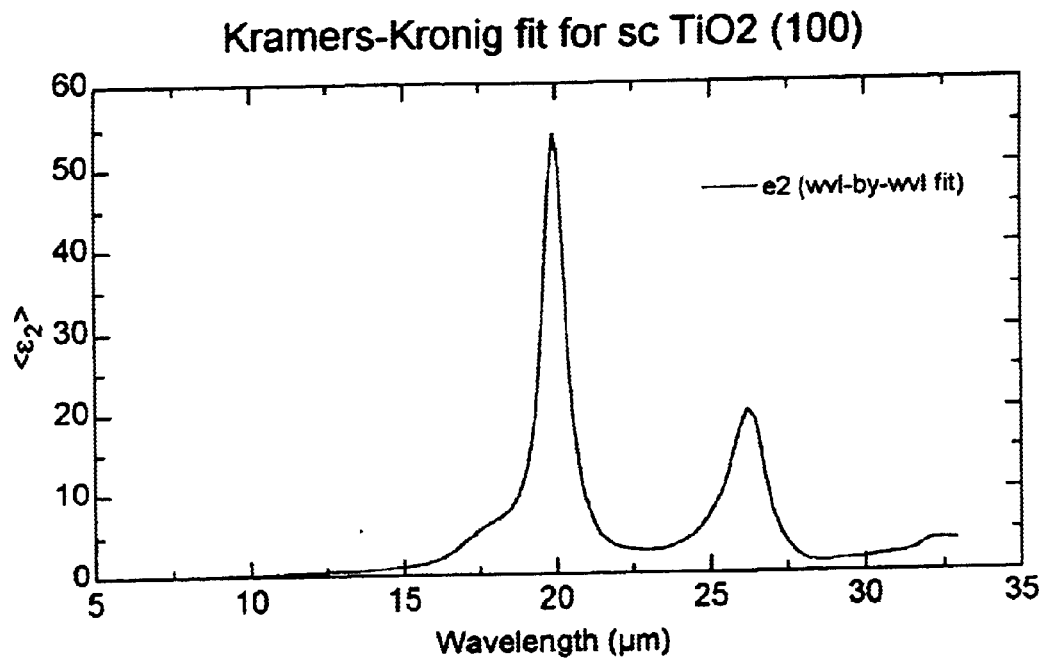
FIG. 7d1
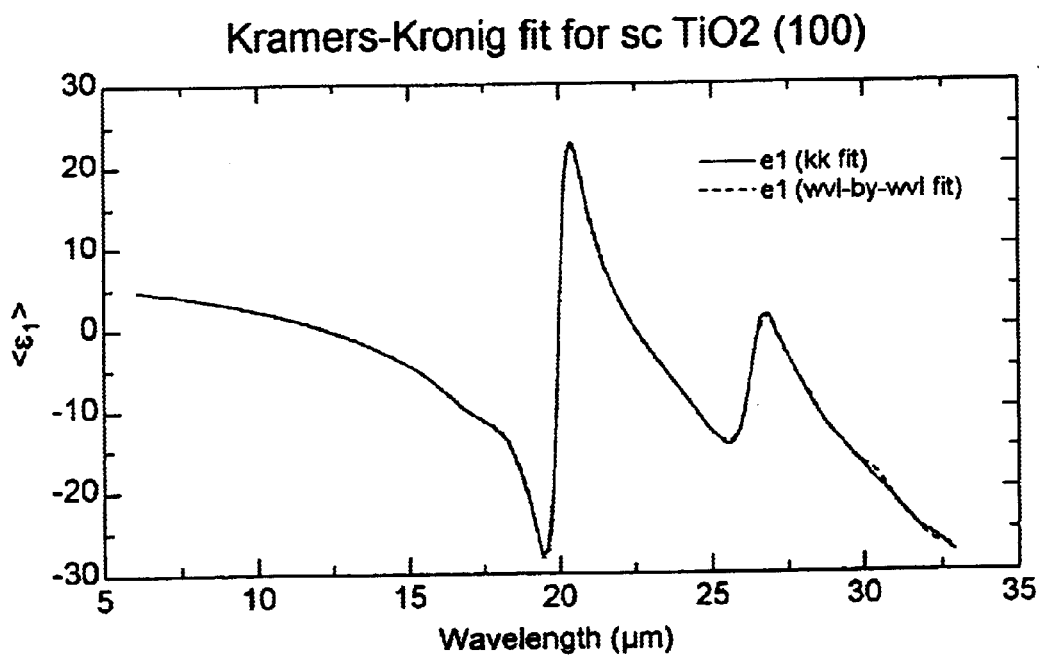
FIG. 7d2

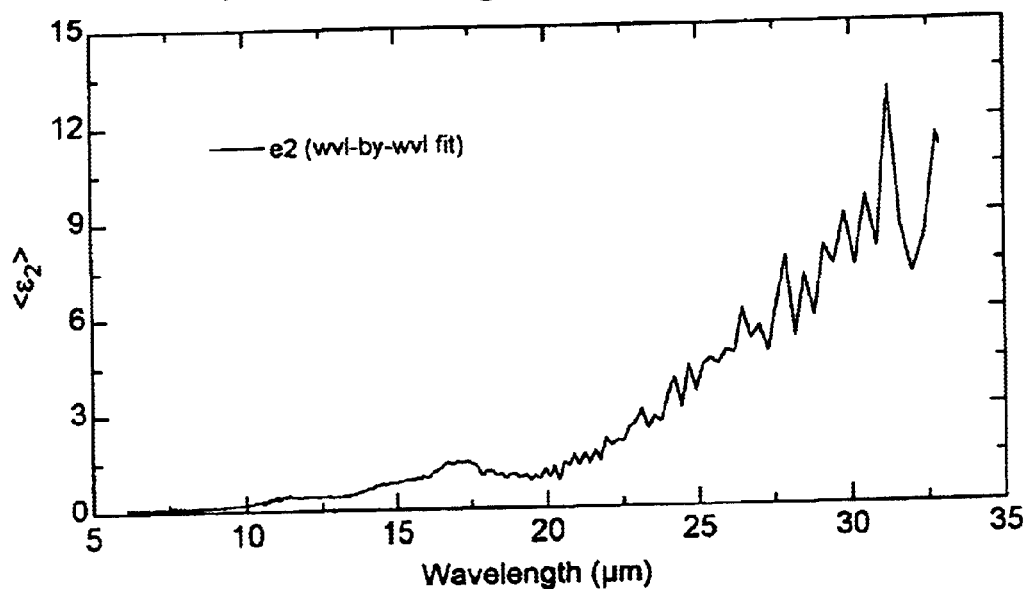
FIG. 7e1
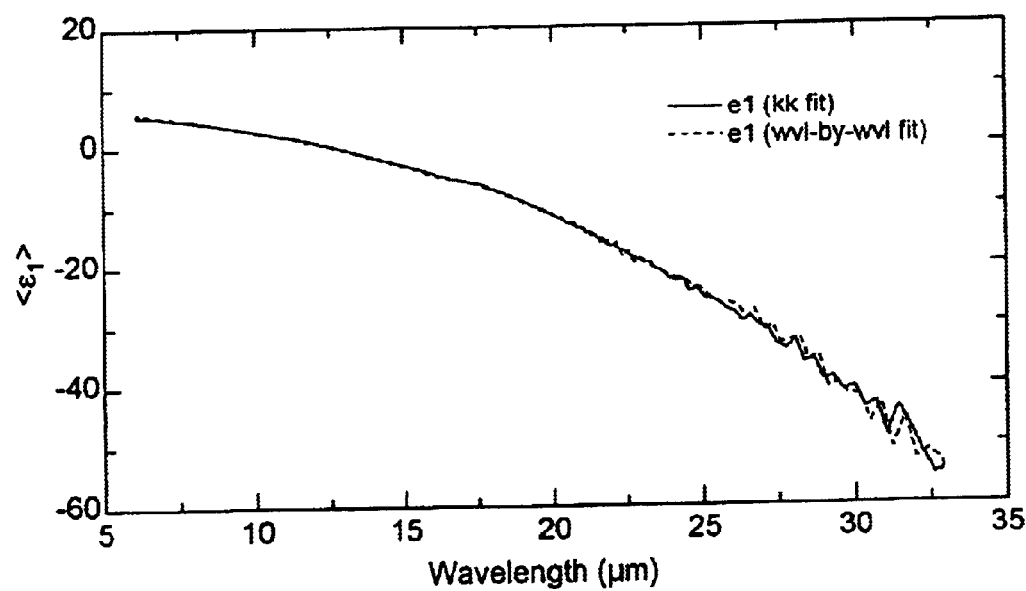
FIG. 7e2

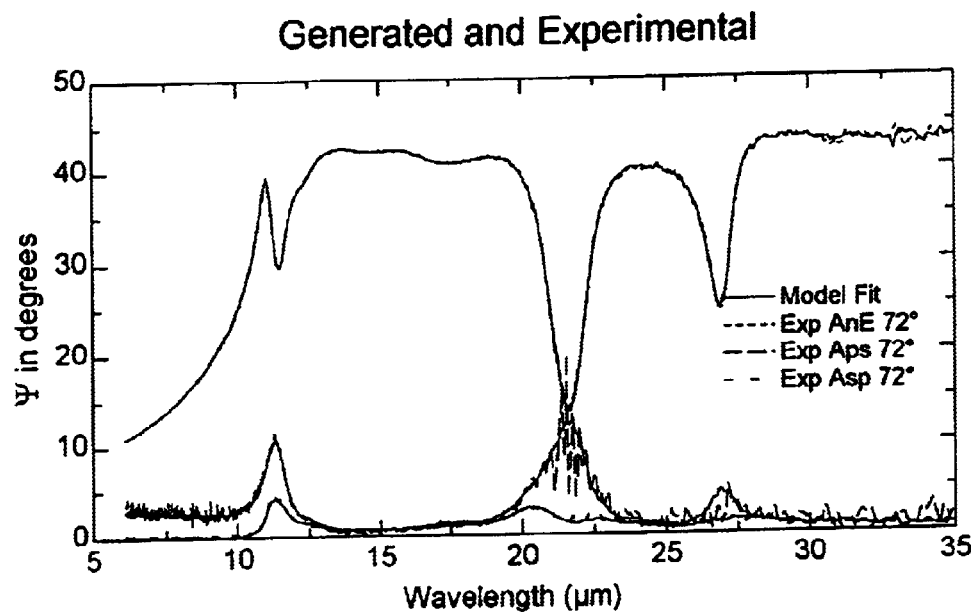
FIG. 8a1
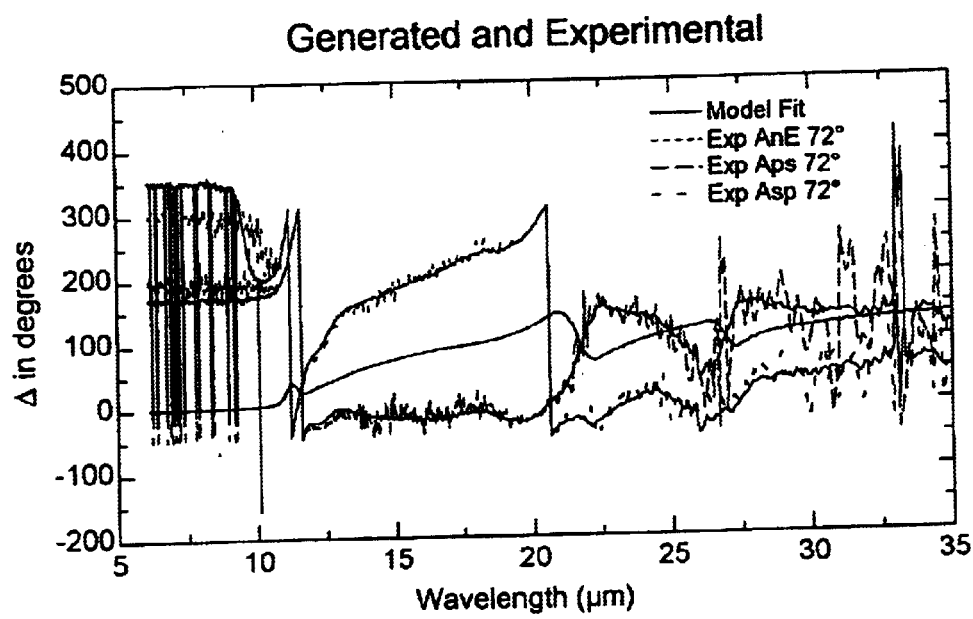
FIG. 8a2

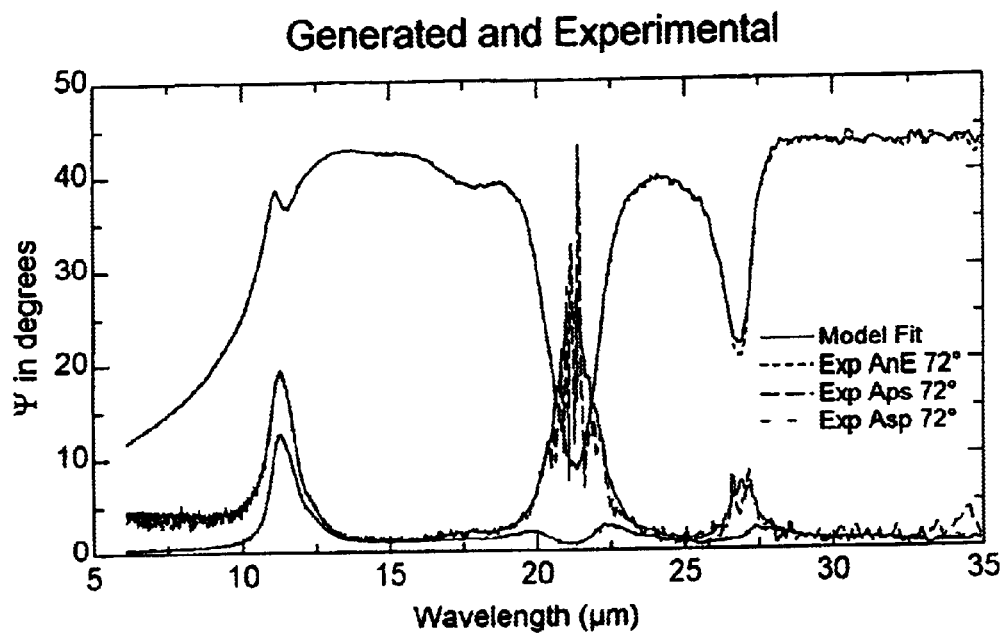
FIG. 8b1
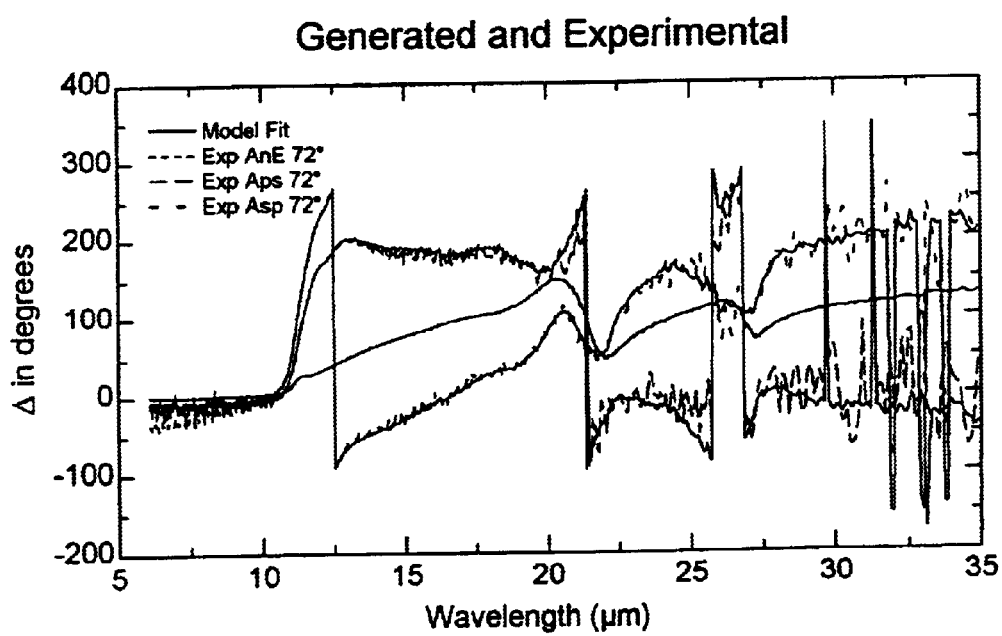
FIG. 8b2

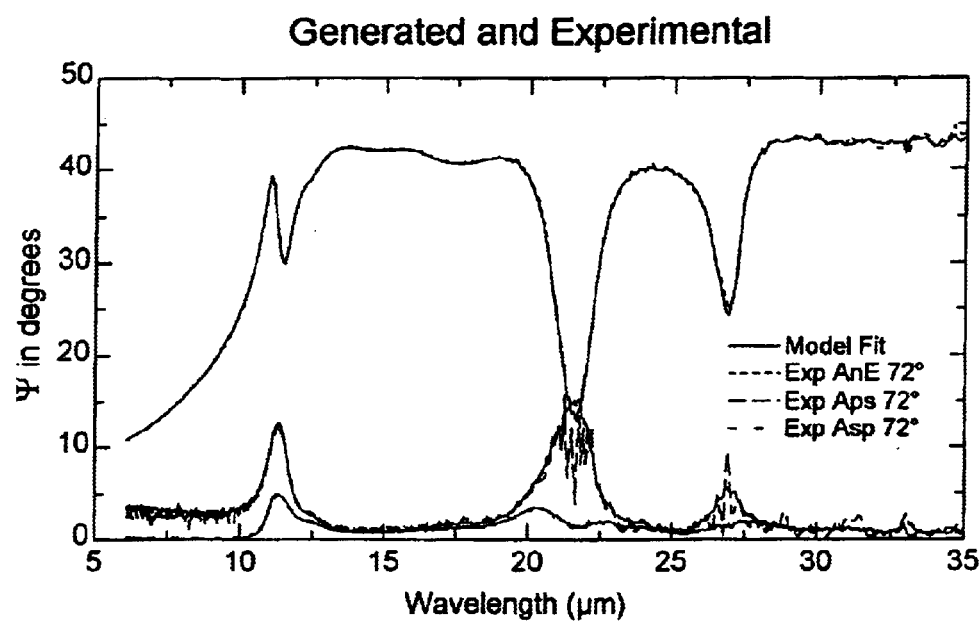
FIG. 8c1
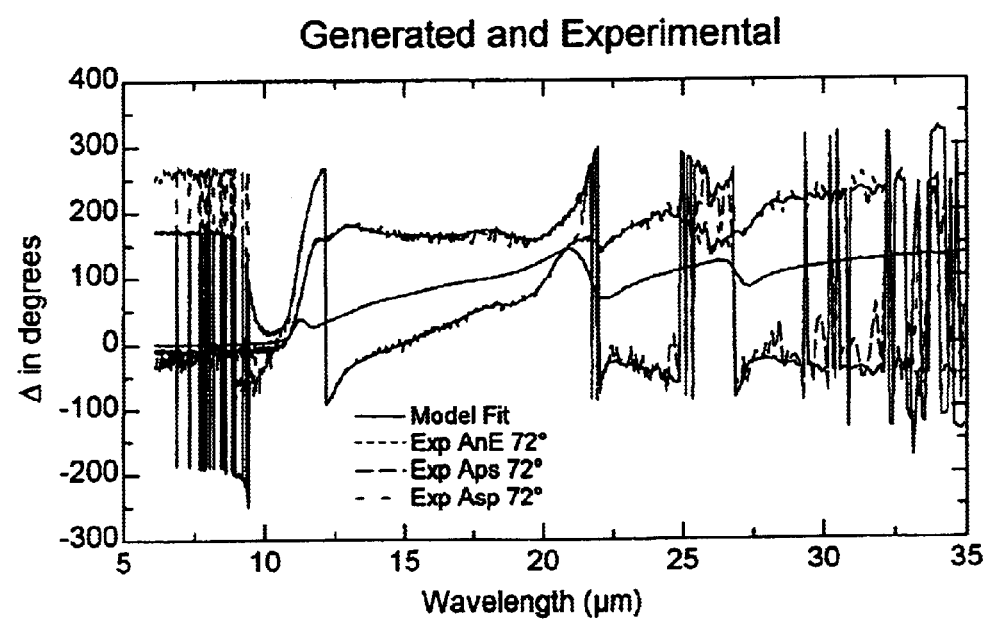
FIG. 8c2

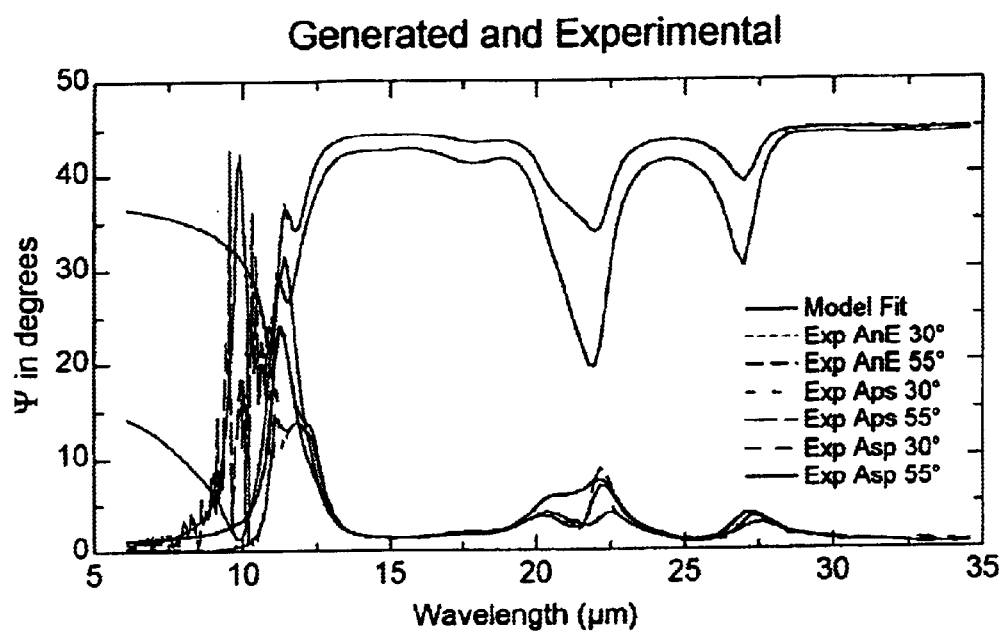
FIG. 8d1
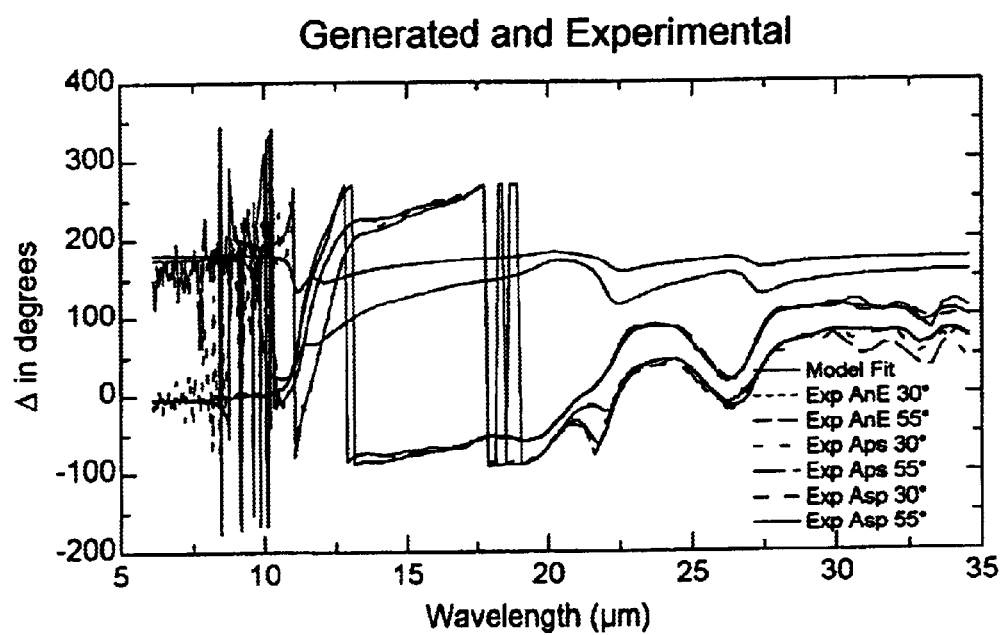
FIG. 8d2

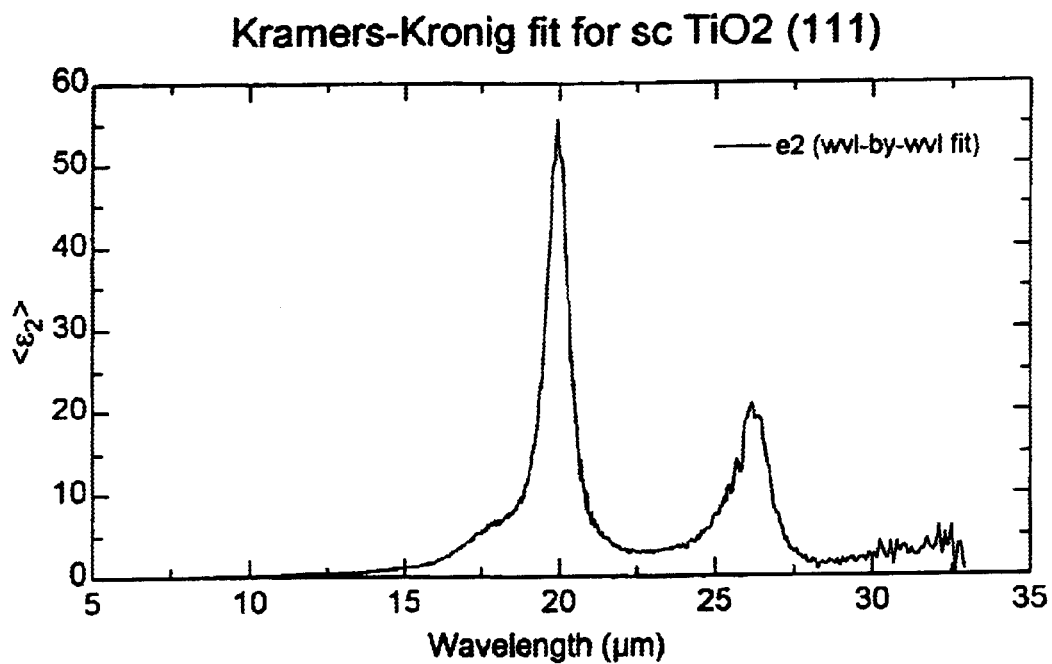
FIG. 8e1
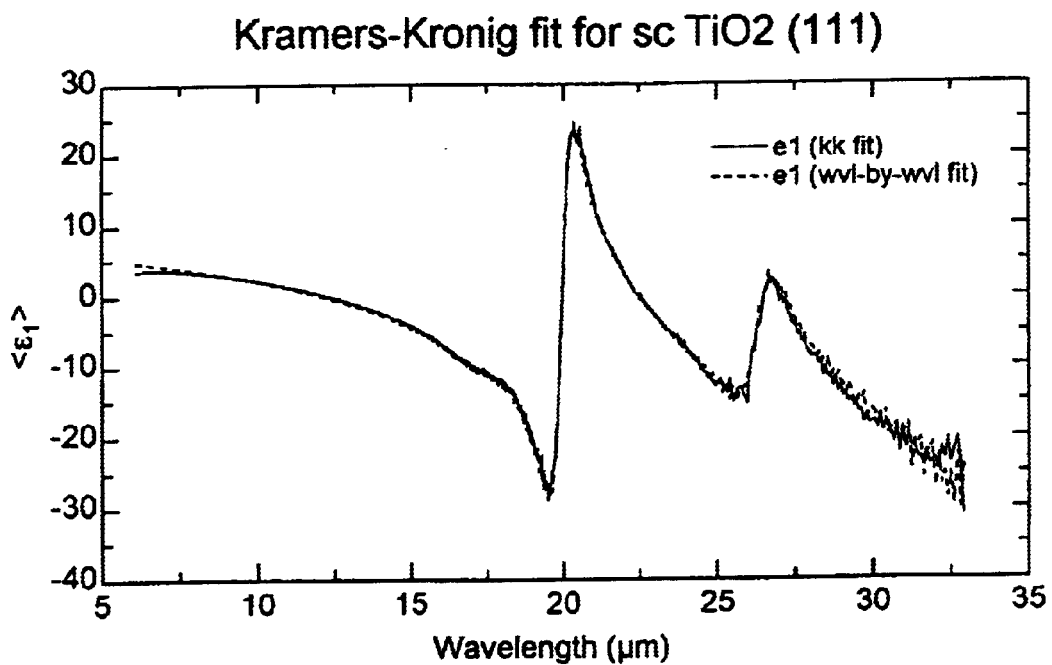
FIG. 8e2

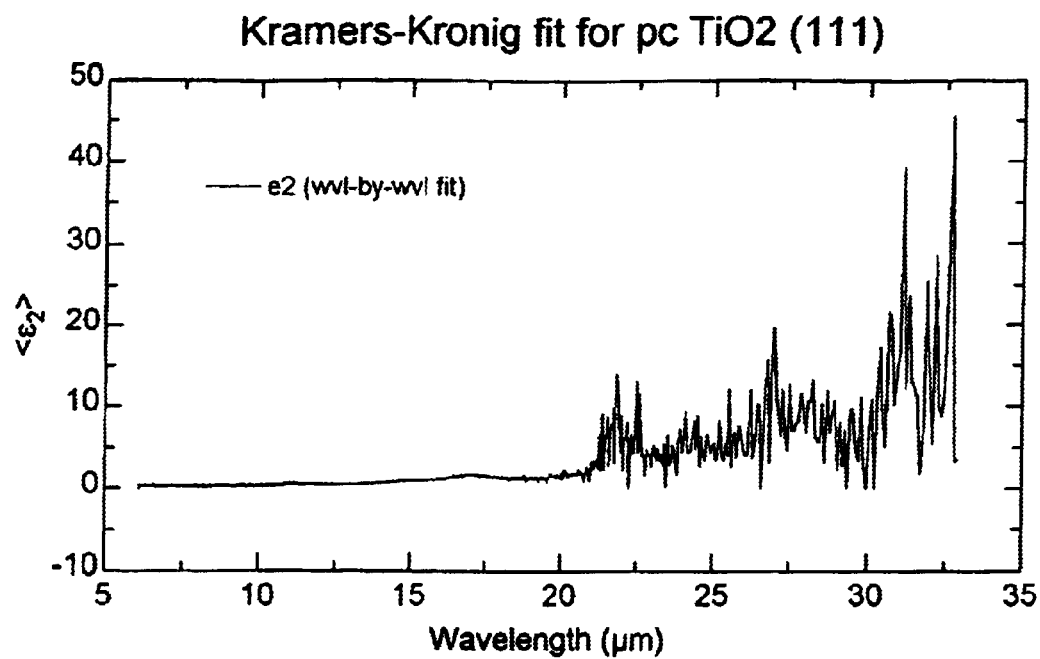
FIG. 8f1
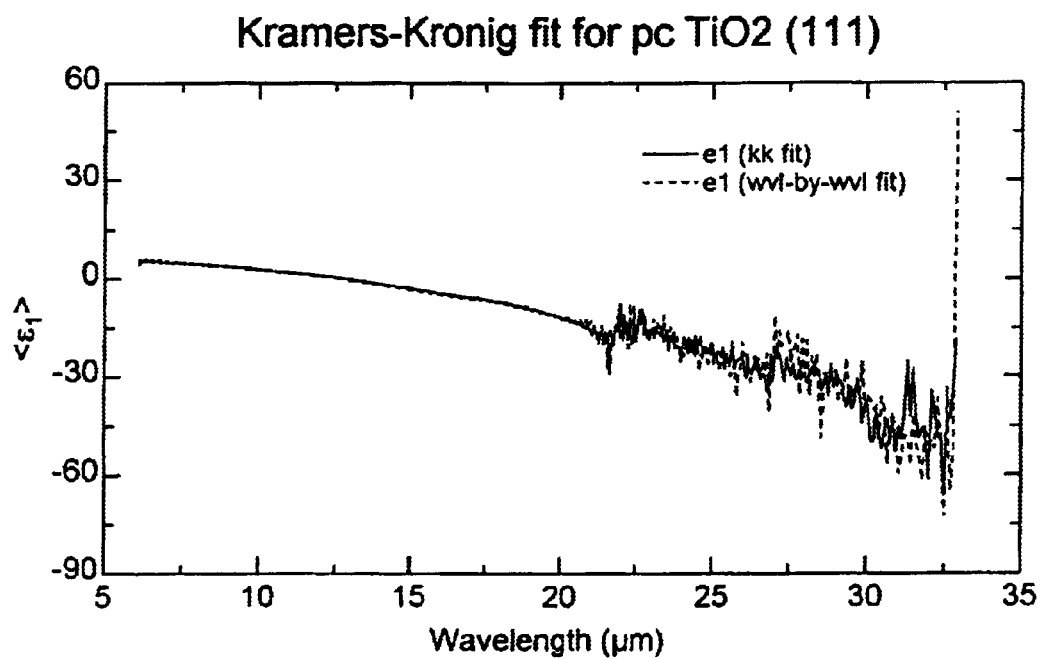
FIG. 8f2

METHOD FOR EVALUATING COMPLEX REFRACTIVE INDICIES UTILIZING IR RANGE ELLIPSOMETRY

This Application is a CIP of Provisional Application Serial No. 60/212,848 filed Jun. 26, 2000, and of Utility Application Serial No. 09/474,318 filed Dec. 29, 1999.

TECHNICAL FIELD

The present invention relates to characterization of optically thick material systems, and more particularly is a method of simultaneously evaluating mathematical model parameters including Euler angles, and directions and magnitudes of complex components of orthogonally related dielectric functions or refractive indicies in an optically thick material system which presents with an optical axis oriented either in-plane or out-of-plane with respect to an alignment surface thereof. The present invention method, while not limited thereto, is particularly applicable in investigating optically thick material systems which are at least uniaxial in that magnitudes of corresponding real, and magnitudes of corresponding imaginary, components of at least two orthogonally related optically thick material system characterizing diagonalized tensor:

$$\overline{\varepsilon}(E) = \begin{bmatrix} \varepsilon_{sc} & 0 & 0 \\ 0 & \varepsilon_{sc} & 0 \\ 0 & 0 & \varepsilon_{pc} \end{bmatrix}$$

complex dielectric functions or refractive indicies are equal.

BACKGROUND

Ellipsometry is a well known means by which to monitor optical and physical properties of material systems, (eg. a substrate which possibly comprises thin films on a surface thereof). In brief, ellipsometry provides that a polarized beam of electromagnetic radiation of one or more wavelengths is caused to impinge upon a material system along one or more angles of incidence and interact, (eg. reflect from or transmit through), therewith. Beams of electromagnetic radiation can be considered as comprised of two orthogonal components, (ie. "P" and "S"), where "P" identifies a plane which contains both an incident beam of electromagnetic radiation, and a normal to an investigated alignment surface of a material system being investigated, and where "S" identifies a plane perpendicular to the "P" plane and parallel to said alignment surface of said material system. A change in polarization state in a polarized beam of electromagnetic radiation caused by said interaction with a material system, is representative of properties of said material system. (Note that Polarization State basically refers to a magnitude of a ratio of orthogonal component magnitudes in a polarized beam of electromagnetic radiation, and a phase angle therebetween, although absolute values for orthogonal components and "handedness", and even percent of polarization are further full polarization state determining factors). Generally two well known angles, (PSI and DELTA), which characterize a material system at a given Wavelength and Angle-of-Incidence, are determined by analysis of data which represents change in polarization state. PSI is a ratio of the "P" and "S" component magnitudes, and DELTA is the phase angle therebetween.

For general interest, it is noted that spectrophotometer systems do not provide data regarding DELTA related phase angle, and often provide absolute, rather than PSI ($\psi$) type ratio, intensity values. For instance, utilizing a transmission Jones matrix:

$$\begin{bmatrix} Epo \\ Eso \end{bmatrix} = \begin{bmatrix} Tpp & Tsp \\ Tps & Tss \end{bmatrix} \begin{bmatrix} Epi \\ Esi \end{bmatrix}$$

to represent mathematically how a material system affects a polarized electromagnetic beam, with Epi and Esi orthogonal components, and which is caused to interact therewith, it is to be appreciated that an ellipsometer/polarimeter system might return an on-diagonal ratio:

$$(Tpp/Tss) = \mathrm{Tan}\left(\psi_{\frac{pp}{ss}}\right)\left(e^{i\Delta_{\frac{pp}{ss}}}\right);$$

and off-diagonal ratios $$(Tsp/Tss) = \mathrm{Tan}\left(\psi_{\frac{sp}{ss}}\right)\left(e^{i\Delta_{\frac{sp}{ss}}}\right);$$

$$(Tps/Tss) = \mathrm{Tan}\left(\psi_{\frac{ps}{ss}}\right)\left(e^{i\Delta_{\frac{ps}{ss}}}\right);$$

$$(Tsp/Tpp) = \mathrm{Tan}\left(\psi_{\frac{sp}{pp}}\right)\left(e^{i\Delta_{\frac{sp}{pp}}}\right);$$

$$(Tps/Tpp) = \mathrm{Tan}\left(\psi_{\frac{ps}{pp}}\right)\left(e^{i\Delta_{\frac{ps}{pp}}}\right);$$

as a function of a selection from the group consisting of:
angle-of-incidence;
wavelength; and
material system rotation about a normal to said alignment surface.

A spectrophotometer system might return Tpp, Tss, Tsp and/or Tps as a function of angle-of-incidence; wavelength; and/or material system rotation about a normal to said alignment surface. It is to be understood that a reflection Jones Matrix $$\begin{bmatrix} Epo \\ Eso \end{bmatrix} = \begin{bmatrix} Rpp & Rsp \\ Rps & Rss \end{bmatrix} \begin{bmatrix} Epi \\ Esi \end{bmatrix}$$

could have also been utilized for said demonstration, and that generally the present invention method can be practiced utilizing data obtained with an ellipsometer system configured in transmission or reflection modes, and/or combinations thereof in any steps thereof, wherein functionality is preserved.

Continuing, Ellipsometer Systems generally include a source of a beam of electromagnetic radiation, a Polarizer, which serves to impose a linear state of polarization on a beam of electromagnetic radiation, a Stage for supporting a material system, and an Analyzer which serves to select a polarization state in a beam of electromagnetic radiation after it has on interacted with a material system, and prior to being passed to a Detector System for analysis. As well, one or more Compensator(s) can be present and serve to affect a phase angle between orthogonal components of a polarized beam of electromagnetic radiation. This is especially important where it is necessary to determine the "Handedness" of a polarized beam of electromagnetic radiation.

A number of types of ellipsometer systems exist, such as those which include rotating elements and those which include modulation elements. Those including rotating elements include Rotating Polarizer (RP), Rotating Analyzer (RA), Rotating Compensator (RC). It is noted that Rotating Compensator Ellipsometer Systems do not demonstrate "Dead-Spots" where obtaining data is difficult. They can read PSI ($\psi$) and DELTA ($\Delta$) of a material system over a full Range of Degrees with the only limitation being that if PSI becomes essentially zero (0.0), one can not then determine DELTA as there is not a sufficient PSI ($\psi$) Polar Vector Length to form the angle between the PSI ($\psi$) Vector and an "X" axis. In comparison, Rotating Analyzer and Rotating Polarizer Ellipsometers have "Dead Spots" at DELTA's ($\Delta$) near 0.0 or 180 Degrees and Modulation Element Ellipsometers also have "Dead Spots" at PSI ($\psi$) near 45 Degrees. The present invention method can be practiced with essentially any ellipsometer system.

A Search of Patents relevant to the present invention has identified very little of specific relevance. One Patent, to Dill, U.S. Pat. No. 4,053,232 describes a Rotating-Compensator Ellipsometer System, which operates utilizes monochromatic light. Two Patents which identify systems which utilize Polychromatic light in investigation of material systems are described in U.S. Pat. Nos. 5,596,406 and 4,668,086, to Rosencwaig et al. and Redner, respectively, were also identified. Also identified is a Patent to Woollam et al, U.S. Pat. No. 5,373,359 as it describes a Rotating Analyzer Ellipsometer System which utilizes white light. Patents continued from the 359 Woollam et al. Patent are, U.S. Pat. Nos. 5,504,582 to Johs et al. and U.S. Pat. No. 5,521,706 to Green et al. Said 582 Johs et al. and 706 Green et al. Patents describe use of polychromatic light in a Rotating Analyzer Ellipsometer System. A Patent to Bernoux et al., U.S. Pat. No. 5,329,357 is identified as it describes the use of optical fibers as input and output means in an ellipsometer system. A Patent to Chen et al., U.S. Pat. No. 5,581,350 is identified as it describes the application of regression in calibration of ellipsometer systems.

A particularly interesting Patent to Herzinger, U.S. Pat. No. 5,835,222, is identified, and incorporated hereinto by reference, as it describes an ellipsometric based method for identifying the orientation of an optical axis in a material system with respect to an alignment surface thereof. One recitation of the method of the 222 Patent method of qualifying a material system as having an optical axis oriented in a desired locus with respect to an alignment surface thereof, comprises, in a functional order, the steps of:

a. by ellipsometric techniques determining the magnitude(s) of at least one member of the group consisting of:

real; imaginary; and a combination of real and imaginary components;

for at least one ratio of components of a material system representing transmission Jones matrix as a function of at least one member of the group consisting of:

wavelength; and

"P" plane angle-of-incidence of an investigating polarized beam of electromagnetic radiation to an alignment surface of said material system; and optical axis radial direction rotation angle;

said at least one ratio of material system representing transmission Jones matrix components being selected from the group consisting of:

on-diagonal ratio (Tpp/Tss);

and off-diagonal ratios (Tsp/Tss);

(Tps/Tss);

(Tsp/Tpp);

(Tps/Tpp);

where Tpp, Tss, Tps and Tsp are the components of a two dimensional material system representing transmission Jones matrix:

$$\begin{bmatrix} Epo \\ Eso \end{bmatrix} = \begin{bmatrix} Tpp & Tsp \\ Tps & Tss \end{bmatrix} \begin{bmatrix} Epi \\ Esi \end{bmatrix}$$

which material system representing transmission Jones matrix describes the change in polarization state between said incident and transmitted portions of said beam of electromagnetic radiation;

b. providing a mathematical model of said material system comprising at least one deviation angle calibration parameter which represents a non-coincidence of said optical axis with a desired locus with respect to said alignment surface, said mathematical model serving to relate indices of refraction, thickness and optical axis direction over a range of at least one member of the group consisting of:

wavelength; and

"P" plane angle-of-incidence of an investigating polarized beam of electromagnetic radiation to an alignment surface of said material system; and optical axis radial direction rotation angle;

c. performing a regression procedure of said mathematical model onto said magnitude of at least one member of the group consisting of:

real;

imaginary; and a combination of real and imaginary components;

of at least one step a. selected ratio of material system representing transmission Jones matrix components as a function of at least one member of the group consisting of:

wavelength;

"P" plane angle-of-incidence of an investigating polarized beam of electromagnetic radiation to an alignment surface of said material system; and optical axis radial direction rotation angle;

such that said at least one deviation angle calibration parameter is evaluated.

Material systems are accepted if the deviation angle is small enough to fall within selected guidelines.

Said method of qualifying a material system as having an optical axis oriented in a desired locus with respect to an alignment surface thereof can further comprising the step of;

e. plotting magnitude(s) of at least one determined on-diagonal (Tpp/Tss) and/or off-diagonal ratio(s) selected from the group consisting of:

(Tps/Tpp) and (Tsp/Tss) and (Tps/Tss) and (Tsp/Tpp);

with respect to at least one parameter selected from the group consisting of:

wavelength;

"P" plane angle-of-incidence of an investigating polarized beam of electromagnetic radiation to an alignment surface of said material system; and optical axis radial direction rotation angle;

and accepting said material system based upon observing said plot(s) only if said plot(s) essentially match known "template" plots.

Another U.S. Pat. No. 5,757,494 to Green et al., is identified as it describes a method for enabling investigation of a material system with ellipsometer systems, even in ellipsometric PSI and/or DELTA regions wherein said ellipsometer system is, without the invention, "blind", (eg. DELTA of (0.0) or (180) degrees) in Rotating Polarizer and Rotating Analyzer Ellipsometer Systems, and/or (PSI or (45) degrees in Modulation Element Ellipsometer Systems). Said 494 Patent describes a method of determination of material system PSI and DELTA values with improved accuracy and precision comprising utilizing a variable compensator, said method comprising in a functional order, the steps of:

a. providing an ellipsometer system selected from the group consisting of:

modulation element, rotatable element and rotating element;

which ellipsometer system enables accurate and precise determination of PSI and DELTA values of essentially any investigatable material system; said ellipsometer system comprising means for setting at least one polarization state in a beam of polarized light and means for identifying, and means for monitoring a polarization state in said polarized beam of light, after an interaction thereof with a material system;

between said means for setting at least one polarization state in a beam of polarized light and said means for monitoring a polarization state in said polarized beam of light, there being present at least one adjustable means for controlling an ellipsometric phase angle between orthogonal components in a polarized beam of light, which adjustable means for controlling an ellipsometric phase angle, in use, allows sequentially setting a plurality of ellipsometric phase angles between orthogonal components in a polarized beam of light which is caused by said ellipsometer system to interact with a material system, such that in use said ellipsometric phase angle can be set sequentially through a plurality of settings while ellipsometric data is obtained by said means for monitoring a polarization state in said polarized beam of light at at least two selected settings of said at least one adjustable means for controlling an ellipsometric phase angle; which obtained ellipsometric data can be utilized in determination of PSI and DELTA values of an investigated material system, where said determination of said PSI and DELTA values includes compensating for the effects on said obtained ellipsometric data of said at least two selected setting of said at least one adjustable means for controlling an ellipsometric phase angle, on said obtained ellipsometric data;

said ellipsometer system being further comprised of computational means which performs determination of investigated material system PSI and DELTA values, which computational means utilizes data obtained with said at least one adjustable means for controlling ellipsometric phase angle between orthogonal components in a polarized beam of light, being set to at least two selected settings, and which computational means performs compensation of the effects of said at least one adjustable means for controlling ellipsometric phase angle between orthogonal components, on said utilized ellipsometric data obtained at said at least two selected settings of said at least one adjustable means for controlling ellipsometric phase angle between orthogonal components, in determining material system PSI and DELTA values;

b. placing a material system to be investigated into said ellipsometer system and causing a beam of polarized light from said means for setting at least one polarization state in a beam of polarized light to interact therewith and enter said means for monitoring a polarization state;

c. adjusting said at least one adjustable means for controlling ellipsometric phase angle between said orthogonal components to be sequentially set to a plurality of settings while ellipsometric data is obtained by said means for monitoring a polarization state in said polarized beam of light at at least two selected settings from said plurality settings of said at least one adjustable means for controlling a value of ellipsometric phase angle between said orthogonal components;

d. causing said computational means to determine investigated material system PSI and DELTA values by a method which performs compensation of the effects of said at least one adjustable means for controlling ellipsometric phase angle between orthogonal components in a polarized beam of light on said ellipsometric data obtained at said at least two selected settings of said at least one adjustable means for controlling ellipsometric phase angle between orthogonal components in a polarized beam of light which is caused to interact with a material system, in determining material system PSI and DELTA values; and e. optionally determining at least some of members of the group consisting of:

the "Handedness";

Stokes Vector; and

Jones and Mueller Matrix components;

of said polarized beam of light and investigated material system.

(It is noted that the computational means can be any computer system with sufficient memory and processing capability).

Said method can include obtaining data comprising a plurality of relative magnitude ratios of orthogonal components and phase angles between orthogonal components are obtained, at least some of which plurality of ellipsometric relative magnitude ratios of orthogonal components and measured ellipsometric phase angles between orthogonal components correspond to sequential adjusted settings of ellipsometric relative magnitude ratios of orthogonal components present in said beam of polarized light, said sequential adjusted settings being effected by adjustment of at least one member of the group consisting of:

said means for setting at least one polarization state in a beam of polarized light; and said means for identifying a polarization state in said polarized beam of light;

and in which said computational means is also caused to perform compensation of the effects of said sequential adjusted settings of ellipsometric relative magnitude ratios of orthogonal components present in said beam of polarized light which is caused by said ellipsometer system to interact with a material system, in determining investigated material system PSI and DELTA values. Said method can also involve obtaining a plurality of ellipsometric phase angles between orthogonal components which are effected at each sequential adjusted setting of ellipsometric relative magnitude ratio of orthogonal components present in said beam of polarized light which is caused by said ellipsometer system to interact with a material system. Said 494 is disclosed as the at least one adjustable means for controlling ellipsometric phase angle between said orthogonal components to be sequentially set to a plurality of settings while ellipsometric data is obtained is a compensator which is typically utilized in practice of the present invention to determine "Handedness", that is, if a value for ($n_{xy}$) which is determined by that invention methodology is positive or negative.

A recent Patent to Johs et al., U.S. Pat. No. 5,872,630, is also disclosed as it describes rotating compensator ellipsometer system and a method of evaluating material system characteristics, involving application of mathematical regression onto data acquired by application of electromagnetic beams thereto. Said 630 Patent Claims a spectroscopic rotating compensator system investigation system comprising a source of a polychromatic beam of electromagnetic radiation, a polarizer, a stage for supporting a material system, an analyzer, a dispersive optics and at least one detector system which contains a multiplicity of detector elements, said spectroscopic rotating compensator material system investigation system further comprising at least one compensator(s) positioned at a location selected from the group consisting of:

before said stage for supporting a material system; and
after said stage for supporting a material system; and
both before and after said stage for supporting a material system;

such that when said spectroscopic rotating compensator material system investigation system is used to investigate a material system present on said stage for supporting a material system, said analyzer and polarizer are maintained essentially fixed in position and at least one of said at least one compensator(s) is caused to continuously rotate while a polychromatic beam of electromagnetic radiation produced by said source of a polychromatic beam of electromagnetic radiation is caused to pass through said polarizer and said compensator(s), said polychromatic beam of electromagnetic radiation being also caused to interact with said material system, pass through said analyzer and interact with said dispersive optics such that a multiplicity of essentially single wavelengths are caused to simultaneously enter a corresponding multiplicity of detector elements in said at least one detector system. Also Claimed is a regression based method of calibrating a spectroscopic rotating compensator material system investigation system comprising the steps of:

a. providing a spectroscopic rotating compensator material system investigation system as described;
b. developing a mathematical model of said spectroscopic rotating compensator material system investigation system which comprises as calibration parameter variables polarizer azimuthal angle orientation, present material system PSI, present material system DELTA, compensator azimuthal angle orientation(s), matrix components of said compensator(s), and analyzer azimuthal angle orientation, which mathematical model is effectively a transfer function which enables calculation of electromagnetic beam intensity as a function of wavelength detected by a detector element, given intensity as a function of wavelength provided by said source of a polychromatic beam of electromagnetic radiation;
c. causing a polychromatic beam of electromagnetic radiation produced by said source of a polychromatic beam of electromagnetic radiation, to pass through said polarizer, interact with a material system caused to be in the path thereof, pass through said analyzer, and interact with said dispersive optics such that a multiplicity of essentially single wavelengths are caused to simultaneously enter a corresponding multiplicity of detector elements in said at least one detector system, with said polychromatic beam of electromagnetic radiation also being caused to pass through said compensator(s) positioned at a location selected from the group consisting of:
before said stage for supporting a material system;
after said stage for supporting a material system; and
both before and after said stage for supporting a material system;

d. obtaining an at least two dimensional data set of intensity values vs. wavelength and a parameter selected from the group consisting of:
angle-of-incidence of said polychromatic beam of electromagnetic radiation with respect to a present material system; and
azimuthal angle rotation of one element selected from the group consisting of:
said polarizer; and
said analyzer;
over time, while at least one of said at least one compensator(s) is caused to continuously rotate;
e. performing a mathematical regression of said mathematical model onto said at least two dimensional data set, thereby evaluating calibration parameters in said mathematical model;
said regression based calibration procedure evaluated calibration parameters serving to compensate said mathematical model for non-achromatic characteristics and non-idealities of said compensator(s), and for azimuthal angles of said polarizer. Said 630 Patent is disclosed for general insight to ellipsometric procedure.

Other Patents to Johs et al. are U.S. Pat. Nos. 5,666,201 and 5,805,285. Said Patents, it is noted, describe, respectively, a spectroscopic ellipsometer and a spectroscopic spectrophotometer system, wherein a spectroscopic beam of electromagnetic radiation is caused to interact with a dispersive optics to the end that multiple orders of wavelengths are produced and detected.

A Patent to Herzinger et al. U.S. Pat. No. 5,796,983 is identified as it describes the Kramers-Kroenig relationship as it applies to novel Dielectric Function Parametric model oscillator structures.

A commonly owned co-pending Patent Application by Hilfiker and Herzinger, describes an ellipsometer/polarimeter, and/or spectrophotometer based method of determining values for anisotropic refractive indices ($n_x$), ($n_y$) and ($n_z$) in, respectively, "x", "y" and "z" directions in a material system, which "x", "y" and "z" directions have a determinable relationship to the orientation of an alignment surface of said material system. Said invention method, in its preferred embodiment, because of its sequence of steps and utilization of parameter values and/or data acquired in earlier steps in later steps, requires acquisition of relatively simple and easy to acquire data sets of only one (1) dimension where refractive indices ($n_x$), ($n_y$) and ($n_z$) or differences therebetween ($\Delta n_{xy}$); and ($\Delta n_{xz}$) or ($\Delta n_{yz}$) are evaluated. However, variations of said preferred method allow for use of multiple dimension data sets in mathematical regression based determination of deviation from perpendicular to a material system alignment surface regarding the direction of an out-of-plane ($n_z$) refractive index, or where, for instance, separately identifiable steps are combined, or where it is desired to determine dispersion characteristics of one or more refractive indices which have previously been evaluated at a single wavelength. The essence of the preferred present invention method can be recited as sequentially involving at least four basic steps, said four basic steps being:

1.

Determining the precise orientation of a third orthogonal index ($n_z$) of refraction which projects essentially perpendicular to an alignment surface of a material system, said alignment surface being characterized by two essentially in-plane orthogonal, (ie. ($n_x$) and ($n_y$)), indices of refraction;

2.

Causing a spectroscopic beam of electromagnetic radiation originating from a source of a beam of electromagnetic radiation, (which spectroscopic beam of electromagnetic radiation is preferably essentially linearly polarized and is comprised of a plurality of wavelengths for which said material system is essentially transparent), to approach said alignment surface of said material system along a locus which is essentially co-incident with the orientation of the third orthogonal index ($n_z$) of refraction, at least partially transmit through said material system and enter a transmission detector to the end that a one-dimensional data set as a function of wavelength is acquired; and applying a computational means which is programmed with a mathematical model for said material system to the end that a value for the difference between the in-plane ($\Delta n_{xy}$) indices of refraction and the Euler angle orientations of said essentially in-plane orthogonal ($n_x$) ($n_y$) indices of refraction are determined;

3.

Causing a beam of electromagnetic radiation originating from said source of a beam of electromagnetic radiation, (which beam of electromagnetic radiation is preferably essentially linearly polarized and is comprised of at least one wavelength), to approach said alignment surface of said material system along a plurality of near normal angles-of-incidence to said material system alignment surface, interact with said material system and enter said transmission and/or reflection detector to the end that a one dimensional data set as a function of angle-of-incidence is acquired; and applying said computational means which is programmed with a mathematical model for said material system to the end that a value for the difference between at least one out-of-plane combination of indices of refraction selected from the group consisting of ($\Delta n_{xz}$), and ($\Delta n_{yz}$) is determined; and

4.

Causing a beam of electromagnetic radiation originating from said source of a beam of electromagnetic radiation, (which beam of electromagnetic radiation is preferably essentially linearly polarized and is comprised of at least one wavelength), to approach said alignment surface of said material system along a plurality of angles-of-incidence at near the Brewster condition to said material system alignment surface, interact with said material system and enter said reflection and/or transmission detector to the end that data as a function of angle-of-incidence is acquired; and applying said computational means which is programmed with a mathematical model for said material system to the end that an absolute value for at least one index of refraction selected from the group consisting of ($n_x$), ($n_y$) and ($n_z$) is/are directly determined, and, if desired or required, from previously determined values for ($\Delta n_{xy}$), ($\Delta n_{xz}$) and ($\Delta n_{yz}$), determining absolute values for ($n_x$), ($n_y$) or ($n_z$) not directly evaluated. The present invention methodology is basically different in that it does not require precise determination of the precise orientation of a third orthogonal index ($n_z$) of refraction which projects essentially perpendicular to an alignment surface of a material system.

The present invention methodology is complementary to that in the pending Hilfiker et al. Application.

Scientific articles which are of direct interest, and which are included herewithin by reference are:

"Optical Characterization Of Anisotropic Plastics", Hilfiker, Herzinger, Bungay, Woollam & Elman, Optical Interference Coatings, Op. Soc. Am, Tech. Dig. Series, Vol. 9, ((1998).

"Characterization of Bi-Axially-Stretched Plastic Films By Generalized Ellipsometry", Elman, Greener, Herzinger & Johs, Thin Solid Films, 313–314 (1998).

"Phase And Microstructure Investigations Of Boron Nitride Thin Films By Spectroscopic Ellipsometry In The Visible And Infrared Spectral Range", Franke, Schubert, Neumann, Tiwald, Thompson, Woollam, Hahn & Richter, J. Appl. Phys. 82(6), (September 1997).

"Determination Of Optical Anisotropy In Calcite From Ultraviolet To Mid-Infrared By Generalized Ellipsometry", Thompson, DeVries, Tiwald, & Woollam, Thin Solid Films, 313–314 (1998).

Additionally, an article by Johs, titled "Regression Calibration Method For Rotating Element Ellipsometers", which appeared in Thin Film Solids, Vol. 234 in 1993 is also identified as it predates the Chen et al. 350 Patent and describes an essentially similar approach to ellipsometer calibration. An article by Jellison Jr. titled "Data Analysis for Spectroscopic Ellipsometry", Thin Film Solids, 234, (1993) is identified as it describes a method for determining the accuracy with which certain data points can be measured, which information allows adding a weighting factor to a curve fitting regression procedure as applied to a multiplicity of data points, said weighting factor serving to emphasize the effect of more accurate and precise data. A book by Azzam and Bashara titled "Ellipsometry and Polarized light" North-Holland, 1977 is disclosed and incorporated herein by reference for general theory. An article by Collins titled "Automated Rotating Element Ellipsometers: Calibration, Operation, and Real-Time Applications", Rev. Sci. Instrum. 61(8), August 1990 is identified as it provides insight into rotating element ellipsometers. An article by Kleim et al. titled "Systematic Errors in Rotating-Compensator Ellipsometry" published in J. Opt. Soc. Am./Vol. 11, No. 9, September 1994 is identified as it describes calibration of rotating compensator ellipsometers. An Article by An and Collins titled "Waveform Analysis With Optical Multichannel Detectors: Applications for Rapid-Scan Spectroscopic Ellipsometer", Rev. Sci. Instrum., 62 (8), August 1991 is also identified as it discusses effects such as Detection System Error Characterization, Stray Light, Image Persistence etc., and calibration thereof. Also disclosed are articles by Schubert et al. which describe "Generalized Ellipsometry". The first thereof is titled "Extension Of Rotating-Analyzer Ellipsometry To Generalized Ellipsometry: Determination Of The Dielectric Function Tensor From Uniaxial TiO2", J. Opt. Soc. Am. A. 13, (1996). This article describes methodology for evaluating all components of a Mueller Matrix dielectric function, but does not describe first diagonalizing said Mueller Matrix and evaluating components of only the three resulting complex dielectric functions or refractive indicies. The second such article is authored by M. Schubert alone and is titled "Polarization Dependent Parameters Of Arbitrary Anisotropic Homogeneous Epitaxial Systems", Phys. Rev. B 53, (1996). The third such article is titled "Generalized Transmission Ellipsometry For Twisted Biaxial Dielectric Media: Application To Chiral Liquid Crystals", J. Opt. Soc. Am. A/Vol. 13, No. 9 (1996). The Schubert et al. articles, it is noted, describe ellipsometer systems which have rotatable material system supporting stages, and primarily focus on investigation of material systems, utilizing said ellipsometer systems, which, (in general terms), material systems have isotropic "in-plane" refractive indices, (ie. where $n_x=n_y$). Further identified for authority regarding mathematical regression is a book titled Numerical Recipes in "C", 1988, Cambridge University Press.

It is noted at this point that the present invention is primarily a method of evaluating directions, and magnitudes of Euler angles and real and imaginary components, of orthogonally related Kramers-Kroenig consistent complex refractive indicies in optically thick material systems which present with an optical axis oriented either in-plane or out-of-plane, with respect to an alignment surface thereof. The present invention methodology works particularly well on optically thick material systems which are "uniaxial", in that corresponding real, and corresponding imaginary, components of at least two orthogonally related optically thick material system characterizing diagonalized tensor:

$$\overline{\varepsilon}(E) = \begin{bmatrix} \varepsilon_{sc} & 0 & 0 \\ 0 & \varepsilon_{sc} & 0 \\ 0 & 0 & \varepsilon_{pc} \end{bmatrix}$$

complex dielectric functions or refractive indicies are of equal magnitude, said two entries being termed "ordinary", with the third entry being termed "extraordinary". (Note, the terminology "ordinary" and "extraordinary" have particular relevance, for instance, where an optically thick material system is composed from a molecular lattice, the molecules of which have a longitudinal "c" axis and two orthogonally oriented axes an "a" plane. A dielectic function or refractive index aligned with the "c" axis, (which is generally the optical axis), is termed "extraordinary", while the dielectric functions or refractive indicies associated with the two orthogonally oriented axes can are termed "ordinary").

Further, it is beneficial to note that randomly measured dielectric function or refractive index tensors which characterize a material system generally contain non-zero values in many of the six off-diagonal entries therein. Well known Matrix mathematical technique, however, provides that such matrices can be "diagonalized", thereby resulting in a Matrix which has non-zero entries only along a top-left to bottom-right diagonal. Matrix Diagonalization involves evaluating Eigenvalues of a given Matrix (M), then forming a Matrix (S) from columns of Matrices in which Eigenvalues are substituted thereinto, finding the inverse of the resulting Matrix (S$^{-1}$), and then multiplying (S)(M)(S$^{-1}$). The present invention works best where a Diagonalized Matrix in which the entries on the diagonal are two ordinary and one extraordinary complex refractive index or dielectric function, preferably wherein the two ordinary entries have equal magnitude real and equal magnitude imaginary components so as to be classified as representing a "uniaxial" optically thick material system. Where no diagonal entries have equal magnitude corresponding real, and equal magnitude corresponding imaginary components, a material system represented is termed "biaxial". Again, it is noted that the present invention methodology works particularly well for optically thick material systems which are properly classified as "uniaxial", where acquired data sets applied in dielectric function or refractive index complex component mathematical regression procedures are obtained utilizing a single spectroscopic electromagnetic beam angle-of-incidence, (of said spectroscopic electromagnetic beam to said alignment surface), and two optically thick material system rotation angle, (around a perpendicular to an alignment surface thereof), settings. Of course, data obtained at additional angles-of-incidence and rotational angles can also be utilized in a mathematical regression evaluation of dielectric function or complex refractive index real and imaginary component values, but such is not typically necessary where an optically thick material system is properly classified as "uniaxial", and even where off-diagnoal terms have non-zero values.

Also, as further general background, it is to be appreciated that the terminology "Kramers-Kroenig refractive index consistency" refers to there being a mathematical integration relationship between real and imaginary components in a dielectric function or complex refractive index. That is, where one, (the real or imaginary), component is evaluated by a mathematical regression procedure, the other, (imaginary or real component, respectively), can be calculated therefrom by mathematical integration. In terms of dielectric constants this is demonstrated by the relationship:

$$\varepsilon_1(E) = 1 + \textit{offset} + \frac{A}{E_e^2 - E^2} + \frac{2}{\pi} P \int_0^\infty \frac{E' \varepsilon_2(E')}{E'^2 - E^2} dE'$$

Where this relationship applies, (and it does in all practical cases), the required strength of a data set utilized in mathematical regression evaluation of real and imaginary components can be reduced as evaluating one complex component allows direct integration mediated calculation of the other. Alternatively, a sufficient data set to evaluate both real and imaginary components can be acquired and applied, and the results checked for Kramers-Kroenig consistency. (See Patent to Herzinger et al. U.S. Pat. No. 5,796,983 for additional insight to the Kramers-Kroenig relationship). As the immediately foregoing refers to both refractive indicies and dielectric constants, it is of benefit to point out the refractive indicies and dielectric constants are directly mathematically related by:

given e=e1+ie2
then e$^2$=e1$^2$–e2$^2$+ie1e2
and given n=SQRT(e$^2$)
then n=SQRT((e1$^2$–e2$^2$)+ie1e2) or n=n'+ik
where n'=(e1$^2$–e2$^2$)
k=ie1e2.
where i=SQRT(–1).

Thus, any reference to complex refractive index should be considered equivalent to reference to complex dielectric function, and vice-versa.

It is also noted that a plane of incidence of a beam of electromagnetic radiation to an alignment surface of an optically thick material system includes its direction of propagation locus and a perpendicular to said alignment surface. Thus it can be stated that the angle-of-incidence of said beam of electromagnetic radiation, is the rotation angle between the locus of said beam of electromagnetic radiation and said alignment surface, taken around an axis defined as being both orthogonal to said direction of propagation locus and in the plane of the alignment surface of the optically thick material system.

Further, it is noted that Euler angles describe the orientation of an optical axis of a material system with respect to the measurement geometry frame of reference. The Phi ( ) Euler angle is that rotation angle around the normal to said optically thick material system alignment surface necessary to align the optical axis projection in the alignment surface to the measurement frame of reference. The Theta (θ) Euler angle is the angle of the optical axis in the resulting new coordinate system rotated around the resulting new "x"-axis direction; and the PSI ($\psi$) Euler angle is the angle of the optical axis in this latest resulting new coordinate system rotated around its new "z"-axis.

Finally, the terminology "optically thick" refers to a material system which provides a reflected beam of electromagnetic radiation caused to impinge thereupon, that is comprised primarily of components reflecting from the top surface thereof, and very little if any components reflected from a bottom surface thereof. Optically thick substrates can result from simply providing a very deep substrate in which reflections from a back-side are minimal because of attenuation, or can effectively be the result of making the substrate wedge shaped in cross-section or can effectively achieved by roughening the back side of the substrate. Optically thick dos not necesarily imply the material system is opaque at the wavelengths utilized.

Even in view of the foregoing, a need remains for methodology for application in simultaneously evaluating Euler angles and direction, and magnitudes of complex components of orthogonally related dielectric function or refractive indicies in an optically thick material system, whether the optical axis thereof is oriented in-plane or out-of-plane with respect to an alignment surface thereof, and where said optically thick material system is characterized by three orthogonally related, Kramers-Kroenig consistent, refractive indicies. The method, while not limited to said application, is particularly applicable in the case of "uniaxial" optically thick material systems, wherein two of said three orthogonally related Kramers-Kroenig consistent, optically thick material system characterizing diagonalized tensor:

$$\bar{\varepsilon}(E) = \begin{bmatrix} \varepsilon_{sc} & 0 & 0 \\ 0 & \varepsilon_{sc} & 0 \\ 0 & 0 & \varepsilon_{pc} \end{bmatrix}$$

complex dielectric function or refractive indicies have corresponding real components of equal magnitude and corresponding imaginary components of equal magnitude, (said two entries being termed "ordinary", with the third entry being termed "extraordinary").

DISCLOSURE OF THE INVENTION

The preferred present invention method enables simultaneously evaluating mathematical model Euler Angles and parameters which describe directions, and magnitudes of real and imaginary components, of orthogonally related Kramers-Kroenig consistent complex dielectric functions or refractive indicies in optically thick material systems which present with an optical axis oriented in a selection from the group consisting of:

in-plane; and out-of-plane;

with respect to an alignment surface thereof, said optically thick material system being uniaxial in that corresponding real and corresponding imaginary components of at least two orthogonally related optically thick material system characterizing diagonalized tensor:

$$\bar{\varepsilon}(E) = \begin{bmatrix} \varepsilon_{sc} & 0 & 0 \\ 0 & \varepsilon_{sc} & 0 \\ 0 & 0 & \varepsilon_{pc} \end{bmatrix}$$

complex dielectric functions or refractive indicies are of equal magnitude, said method comprising, in any functional order, the steps of:

a. providing an optically thick material system which presents with Kramers-Kroenig consistent complex dielectric functions or refractive indicies and with an optical axis oriented either in-plane or out-of-plane with respect to an alignment surface thereof, said optically thick material system being uniaxial in that corresponding real and corresponding imaginary components of at least two orthogonally related optically thick material system characterizing diagonalized tensor:

$$\bar{\varepsilon}(E) = \begin{bmatrix} \varepsilon_{sc} & 0 & 0 \\ 0 & \varepsilon_{sc} & 0 \\ 0 & 0 & \varepsilon_{pc} \end{bmatrix}$$

complex dielectric functions or refractive indicies are of equal magnitude;

b. placing said optically thick material system into a system for directing at least one spectroscopic polarized electromagnetic beam(s) of radiation onto said alignment surface at at least one angle(s) of incidence removed from a normal to said alignment surface, said system for directing at least one spectroscopic polarized electromagnetic beam(s) of radiation onto said alignment surface at at least one angle(s) of incidence removed from a normal to said alignment surface comprising a reflection detector system;

c. selecting at least one spectroscopic polarized electromagnetic beam(s) of radiation to at least partially comprise wavelengths for which said optically thick material system is non-transparent, and causing said at least one beam(s) of spectroscopic polarized electromagnetic radiation to impinge on said alignment surface of said optically thick material system, at at least one angle(s) of incidence removed from a normal to said alignment surface, in plane(s) of incidence which include the locus of said beam of spectroscopic polarized electromagnetic radiation and said normal to said alignment surface, said at least one beam(s) of spectroscopic polarized electromagnetic radiation being caused to reflect from said alignment surface of said optically thick material system and into said reflection detector system;

d. at said at least one angle(s) of incidence and at one rotation angle of said optically thick material system around said normal to the alignment surface thereof, obtaining reflection detector system mediated experimental reflection intensity data as a functions of wavelength and angle of incidence of said at least one beam of spectroscopic polarized electromagnetic radiation onto said optically thick material system alignment surface;

e. from the data obtained in step d., determining Jones Matrix:

$$\begin{bmatrix} Epo \\ Eso \end{bmatrix} = \begin{bmatrix} Tpp & Tsp \\ Tps & Tss \end{bmatrix} \begin{bmatrix} Epi \\ Esi \end{bmatrix}$$

components and if the off-diagonal components are essentially zero, rotate the optically thick material system about a perpendicular to the alignment surface thereof, and proceeding to step f. and if not proceeding directly to step g.;

f. at said at least one angle(s) of incidence and at one rotation angle of said optically thick material system around said normal to the alignment surface thereof, obtaining reflection detector system mediated experimental reflection intensity data as a functions of wavelength and angle of incidence of said at least one beam of spectroscopic polarized electromagnetic radiation onto said optically thick material system alignment surface;

g. simultaneously providing a mathematical model of said optically thick material system which includes as parameters therein at least:

real and imaginary components for each of the orthogonally related, Kramers-Kroenig consistent tensor diagonal complex dielectric functions or refractive indicies;

sufficient rotation about a normal to an alignment surface, and deviation from alignment with said alignment surface angle parameters to define the orientations of the orthogonally related, Kramers-Kroenig consistent tensor diagonal complex dielectric functions or refractive indicies, and orientation of the optical axis, with respect to the alignment surface; and Euler angles relating material system angles to a laboratory frame of reference; and h. via application of a mathematical regression technique, evaluating parameters in said mathematical model to provide a best-fit to acquired experimental data.

A modified method of evaluating mathematical model parameters describing Euler angles and directions, and magnitudes of real and imaginary components, of orthogonally related Kramers-Kroenig consistent complex dielectric functions or refractive indicies in an optically thick material system which presents with an optical axis oriented in a selection from the group consisting of:

in-plane; and out-of-plane; with respect to an alignment surface thereof. Said method basically comprises, in any functional order, the steps of:

a. providing an optically thick material system which presents with orthogonally related Kramers-Kroenig consistent complex dielectric functions or refractive indicies and with an optical axis oriented either in-plane or out-of-plane with respect to an alignment surface thereof, said optically thick material system preferably, but not necessarily, being uniaxial in that corresponding real and corresponding imaginary components of at least two orthogonally related optically thick material system characterizing diagonalized tensor:

$$\overline{\varepsilon}(E) = \begin{bmatrix} \varepsilon_{sc} & 0 & 0 \\ 0 & \varepsilon_{sc} & 0 \\ 0 & 0 & \varepsilon_{pc} \end{bmatrix}$$

complex dielectric function or refractive indicies are of equal magnitude;

b. placing said optically thick material system into a system for directing at least one spectroscopic polarized electromagnetic beam(s) of radiation onto said alignment surface at at least one angle(s) of incidence removed from a normal to said alignment surface, said system for directing at least one spectroscopic polarized electromagnetic beam(s) of radiation onto said alignment surface at at least one angle(s) of incidence removed from a normal to said alignment surface comprising a reflection detector system;

c. selecting at least one spectroscopic polarized electromagnetic beam(s) of radiation to at least partially comprise wavelengths for which said optically thick material system is non-transparent, and causing said at least one beam(s) of spectroscopic polarized electromagnetic radiation to impinge on said alignment surface of said optically thick material system, at at least one angle(s) of incidence removed from a normal to said alignment surface, in plane(s) of incidence which include the locus of said beam of spectroscopic polarized electromagnetic radiation and said normal to said alignment surface, said at least one beam(s) of spectroscopic polarized electromagnetic radiation being caused to reflect from said alignment surface of said optically thick material system and into said reflection detector system;

d. at said at least one angle(s) of incidence and at at least two rotation angles of said optically thick material system around said normal to the alignment surface thereof, obtaining reflection detector system mediated experimental reflection intensity data as a function of wavelength and angle of incidence of said at least one beam of spectroscopic polarized electromagnetic radiation onto said optically thick material system alignment surface;

e. simultaneously providing a mathematical model of said optically thick material system which includes as parameters therein at least:

real and imaginary components for each of the orthogonally related, Kramers-Kroenig consistent tensor diagonal complex dielectric function or refractive indicies;

sufficient rotation about a normal to an alignment surface, and deviation from alignment with said alignment surface angle parameters to define the orientations of the orthogonally related, Kramers-Kroenig consistent tensor diagonal complex dielectric function or refractive indicies, and orientation of the optical axis, with respect to the alignment surface; and Euler angles relating material system angles to a laboratory frame of reference;

f. via application of a mathematical regression technique, evaluating parameters in said mathematical model in view of acquired experimental data.

Preferred present invention practice, where in-plane projection directions of two orthogonally related complex dielectric function or refractive indicies are known, involves obtaining experimental reflection data at two rotation angles of said optically thick material system around said normal to the alignment surface thereof, said two rotation angles being appropriate to sequentially align a plane of incidence of said at least one spectroscopic polarized electromagnetic beam of radiation along the direction of an in-plane projection of two of the orthogonally related complex dielectric function or refractive indicies which have equal magnitude corresponding real and equal magnitude corresponding imaginary components.

Alternatively, the present invention method can involve obtaining experimental reflection data at two rotation angles of said optically thick material system around said normal to the alignment surface thereof, where said two rotation angles are appropriate to align a plane of incidence of said at least one spectroscopic polarized electromagnetic beam of radiation along the direction of an in-plane projection of one of said two orthogonally related dielectric function or refractive indicies which have equal magnitude corresponding real and equal magnitude corresponding imaginary components, but also involves obtaining experimental reflection data with said plane of incidence of said at least one beam of spectroscopic polarized electromagnetic radiation oriented along a direction rotationally between the directions of said in-plane projections of said two orthogonally related complex dielectric function or refractive indicies which have equal magnitude corresponding real and equal magnitude corresponding imaginary components.

Further, particularly where an optical axis of an optically thick material system does not project in an alignment surface thereof, or perpendicular to said alignment surface, present invention practice can involve obtaining data sets at multiple, (eg. more than two), rotation angles of said optically thick material system around said normal to the alignment surface thereof, and said rotation angles can be selected to include, or not, orientations which place the plane of incidence of said at least one spectroscopic polarized electromagnetic beam of radiation along the in-plane projection direction of at least one of the two orthogonally related dielectric function or refractive indicies which have equal magnitude corresponding real and equal magnitude corresponding imaginary components. This approach is often necessary as in-plane projection directions of two orthogonally related complex dielectric function or refractive indicies are not known.

It is also noted that in any version of the present invention methodology, the obtaining of experimental reflection intensity data as a function of wavelength and angle of incidence of said at least one beam of spectroscopic polarized electromagnetic radiation onto said optically thick material system alignment surface, can involve obtaining experimental data sets at two or more spectroscopic electromagnetic radiation beam angles of incidence and/or at two or more optically thick material system rotation angles.

It is noted that the mathematical regression technique preferably involves reduction of square-error.

Present invention methodology can involve providing a transmission detector and obtaining transmission data at at least one angle(s) of incidence of said at least one beam of spectroscopic electromagnetic radiation removed from a normal to said alignment surface. This is not in contradiction to the material system "optically thick" designation as "optically thick" does not necessarily indicate opacity of a material system at a utilized wavelength. Rather it refers to a material system which does not significantly reflect incident electromagentic radiation from a back-side thereof.

Additionally, the present invention methodology can involve providing at least two optically thick material systems which each present with orthogonally related Kramers-Kroenig consistent complex dielectric functions or refractive indicies and with an optical axis oriented either in-plane or out-of-plane with respect to an alignment surface thereof, each said optically thick material system being at least uniaxial in that corresponding real and corresponding imaginary components of at least two orthogonally related optically thick material system characterizing diagonalized tensor:

$$\bar{\varepsilon}(E) = \begin{bmatrix} \varepsilon_{sc} & 0 & 0 \\ 0 & \varepsilon_{sc} & 0 \\ 0 & 0 & \varepsilon_{pc} \end{bmatrix}$$

dielectric function or complex refractive indicies are of equal magnitude; said method further comprising, for each said optically thick material system proceeding as described above, wherein said method further comprises, via application of a mathematical regression technique, simultaneously evaluating parameters in said mathematical models for each of the investigated optically thick material systems in view of acquired experimental data.

It is also to be appreciated that the present invention method of simultaneously evaluating Euler angles and directions and magnitudes of real and imaginary components of orthogonally related Kramers-Kroenig consistent complex refractive indicies in an optically thick material system is particularly suited for application where the wavelengths selected at which said optically thick material system is non-transparent, are in the infrared range of 5 to 40 microns.

Finally, it has been determined that a screening step is beneficial to practice of the present invention, said screening step being the evaluating of the components of a Jones Matrix, or equivalent elements of a Mueller Matrix. Only if said step provides Off-Diagonal terms which are not essentially zero (0.0), does one proceed. If said step returns Off-Diagonal terms which are essentially zero (0.0), the additional step of rotating the sample system being investigated is performed so that said Off-Diagonal terms become other than essentially zero (0.0).

The present invention will be better understood by reference to the Detailed Description Section of this Specification, with reference to the Drawings.

SUMMARY OF THE INVENTION

It is a primary purpose and/or objective of the present invention to provide a method of simultaneously evaluating mathematical model parameters describing Euler angles and directions, and magnitudes of orthogonally related complex components of dielectric function or refractive indicies in a optically thick material system which presents with an optical axis oriented either in-plane or out-of-plane with respect to an alignment surface thereof, said optically thick material system preferably, but not necessarily, being at least:

uniaxial;

in that magnitudes of corresponding real, and magnitudes of corresponding imaginary, components of at least two orthogonally related optically thick material system characterizing diagonalized tensor:

$$\bar{\varepsilon}(E) = \begin{bmatrix} \varepsilon_{sc} & 0 & 0 \\ 0 & \varepsilon_{sc} & 0 \\ 0 & 0 & \varepsilon_{pc} \end{bmatrix}$$

complex dielectric function or refractive indicies are equal.

It is another purpose and/or objective of the present invention to, via acquisition and application of additional data, extend the present invention method of evaluating mathematical model parameters describing Euler angles and directions, and magnitudes of orthogonally related complex components of dielectric function or refractive indicies in an optically thick material system which presents with an optical axis oriented either in-plane or out-of-plane with respect to an alignment surface thereof, to cases where said optically thick material system is:

biaxial;

in that no magnitudes of corresponding real, and magnitudes of corresponding imaginary, components of at least two orthogonally related optically thick material system characterizing diagonalized tensor:

$$\bar{\varepsilon}(E) = \begin{bmatrix} \varepsilon_{sc} & 0 & 0 \\ 0 & \varepsilon_{sc} & 0 \\ 0 & 0 & \varepsilon_{pc} \end{bmatrix}$$

complex dielectric function or refractive indicies are equal.

It is another purpose and/or objective of the present invention to, via acquisition and application of additional data, extend the present invention method of evaluating mathematical model parameters describing Euler angles and directions, and magnitudes of orthogonally related complex components of dielectric function or refractive indicies in an optically thick material system which presents with an optical axis oriented either in-plane or out-of-plane with respect to an alignment surface thereof, to cases where said optically thick material system is non-diagonal in that off-diagonal components of a optically thick material system characterizing tensor are non-zero.

It is another purpose and/or objective of the present invention to teach applying a preliminary screening step is beneficial to practice of the present invention, said screening step being the evaluating of the components of a Jones Matrix, or equivalent elements of a Mueller Matrix. Only if said step provides Off-Diagonal terms which are not essentially zero (0.0), does one proceed. If said step returns Off-Diagonal terms which are essentially zero (0.0), the additional step of rotating the sample system being investigated is performed so that said Off-Diagonal terms become other than essentially zero (0.0).

Other purposes and/or objectives will become appearant by a reading of the Specification and Claims.

BRIEF DESCRIPTION OF THE DRAWINGS

FIGS. 4a–4d demonstrate Miller indicies of crystals cut (110), (111), (111) and (221).

FIG. 5a shows an optically thick material system and a beam of electromagnetic radiation oriented in a plane which directs it along the x-axis direction of a rectangular bulk $TiO_2$.

FIGS. 6a1–6c2 show PSI and DELTA data for (110) orientation $TiO_2$ derived by regression onto data sets which were simultaneously applied in a wavelength by wavelength regression fit to provide the real and imaginary sc and pc dielectric function values shown in FIGS. 6d1–6e2.

FIGS. 6d1 and 6d2 show complex dielectric sc components ($\epsilon_1$) and ($\epsilon_2$) arrived at by simultaneous wavelength by wavelength regression onto data sets used to provide results shown in FIGS. 6a1–6c2.

FIGS. 6e1 & 6e2. show complex dielectric pc components ($\epsilon_1$) and ($\epsilon_2$) arrived at by simultaneous wavelength by wavelength regression onto data sets used to provide results shown in FIGS. 6a1–6c2.

FIGS. 7a1–7c2 show PSI and DELTA data for (100) orientation $TiO_2$ derived by regression onto data sets which were simultaneously applied in a wavelength by wavelength regression fit to provide the real and imaginary sc and pc dielectric function values shown in FIGS. 7d1–7e2.

FIGS. 7d1 and 7d2 show complex dielectric sc components ($\epsilon_1$) and ($\epsilon_2$) arrived at by simultaneous wavelength by wavelength regression onto data sets used to provide results shown in FIGS. 7a1–7c2.

FIGS. 7e1 & 7e2. show complex dielectric pc components ($\epsilon_1$) and ($\epsilon_2$) arrived at by simultaneous wavelength by wavelength regression onto data sets used to provide results shown in FIGS. 7a1–7c2.

FIGS. 8a1–8d2 show PSI and DELTA data for (111) orientation $TiO_2$ derived by regression onto data sets which were simultaneously applied in a wavelength by wavelength regression fit to provide the real and imaginary sc and pc dielectric function values shown in FIGS. 8e1–8f2.

FIGS. 8e1 and 8e2 show complex dielectric sc components ($\epsilon_1$) and ($\epsilon_2$) arrived at by simultaneous wavelength by wavelength regression onto data sets used to provide results shown in FIGS. 8a1–8d2.

FIGS. 8f1 and 8f2 show complex dielectric sc components ($\epsilon_1$) and ($\epsilon_2$) arrived at by simultaneous wavelength by wavelength regression onto data sets used to provide results shown in FIGS. 8a1–8d2.

DETAILED DESCRIPTION

Figure 1:
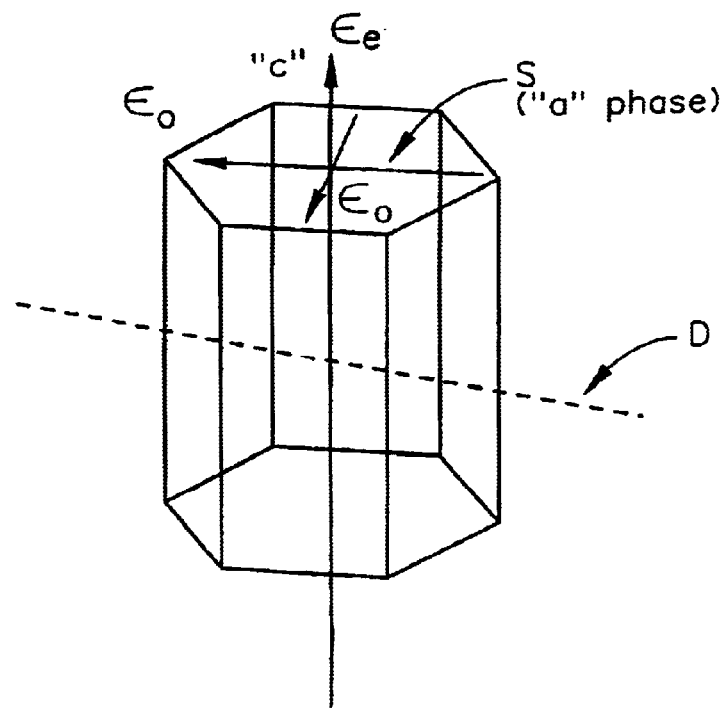
FIG. 1 shows a demonstrative Hexagonal Lattice structure with a "c" axis shown oriented vertically, and an "a" plane oriented orthogonal thereto.
Figure 2:
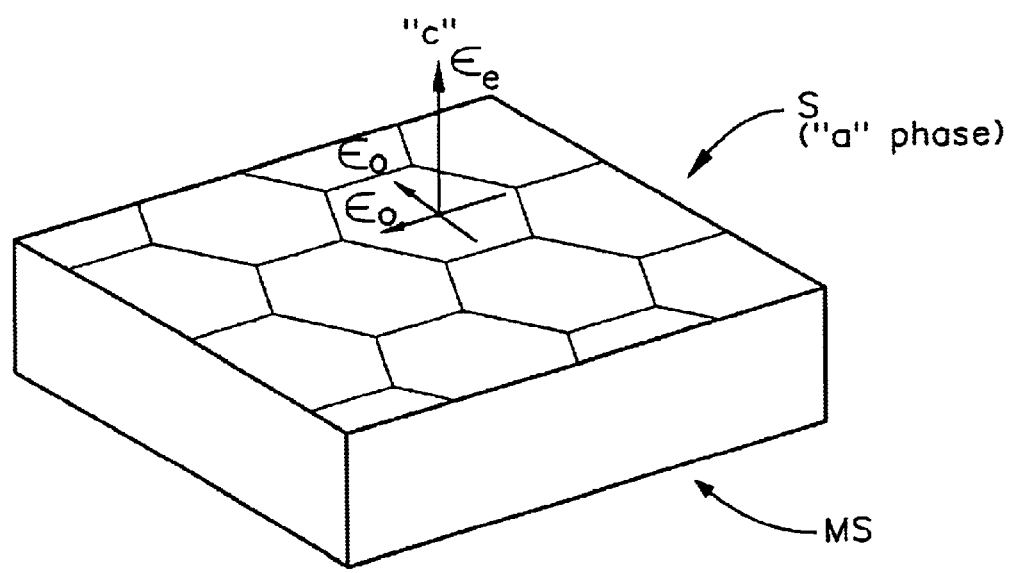
FIG. 2 shows that an optically thick material system arrangement realized by positioning a multiplicity of such hexagonal lattice structures horizontally lateral to one another.
Figure 3A:
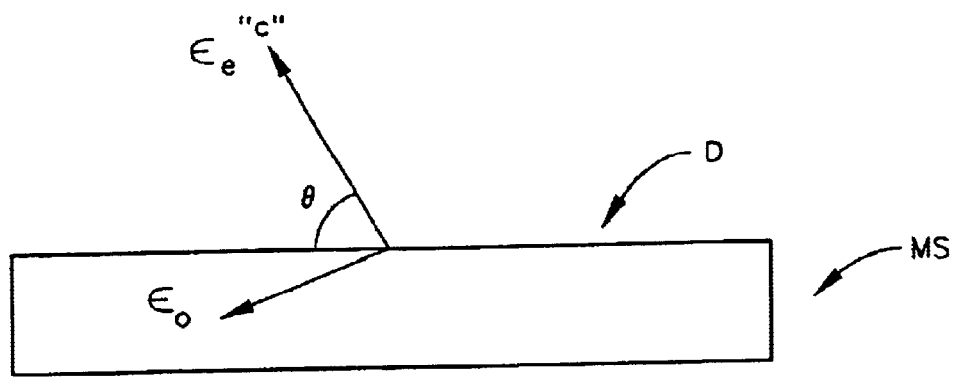
FIG. 3a demonstrates a side view of such an optically thick material system shoving an extraordinary dielectric function projecting other than perpendicular to the surface (D), and one ordinary dielectric function projecting other than parallel to the surface (D).

Turning now to FIG. 1, there is shown a demonstrative Hexagonal Lattice structure with a "c" axis shown oriented vertically, and an "a" plane oriented orthogonal thereto. Also shown is an extraordinary dielectric function or refractive index ($\epsilon_e$) oriented along said "c" axis, and two orthogonal "ordinary" refractive indices ($\epsilon_e$) in a Surface (S). FIG. 2 shows that a simply arrived-at optically thick material system arrangement might be realized by positioning a multiplicity of such hexagonal lattice structures horizontally lateral to one another, and in such a simple optically thick material system the "c" axis, and coincident extraordinary dielectric function or refractive index are perpendicular to the surface (S), and the ordinary refractive indicies are "in-plane" with respect to the surface (S). In such a simply arrived-at optically thick material system the surface (S) can be considered an Alignment Surface. Proceeding, said simply arrived-at optically thick material system could be cut along an angle to said surface (S) provide an optically thick material system with an alignment surface which is not coincident with the surface (S). That is, the lattice orientations in said optically thick material system would oriented so as to place said "c" axis and extraordinary refractive index direction other than perpendicular to a bulk physical optically thick material system alignment surface. It can be visualized, however, that were such a bulk optically thick material system as shown in FIG. 2, cut along a diagonal (D) as shown in FIG. 1, that an bulk optically thick material system "alignment surface" would result in which the "c" axis and extraordinary refractive index direction would not project perpendicular thereto, and in which the ordinary refractive indicies would not project in-plane with said "alignment surface". FIG. 3a demonstrates a side view of such a resulting optically thick material system showing an extraordinary dielectric function or refractive index projecting other than perpendicular to the surface (D), and one ordinary refractive index projecting other than parallel to the surface (D). Many such scenarios can be developed, and generally well known Miller indicies are utilized to designate how crystals are cut to arrive at various orientations. FIGS. 4a–4d demonstrate Miller indicies of crystals cut (110), (111), (111) and (221) respectively, and it can be determined that the approach to determining Miller indices involves identifying where a plane intercepts "x", "y" and "z" axes, then dividing that value into 1. A (100) plane would then intercept the "x" axis at 1.0 and be parallel to the "y"-"z" plane.

Figure 3B:
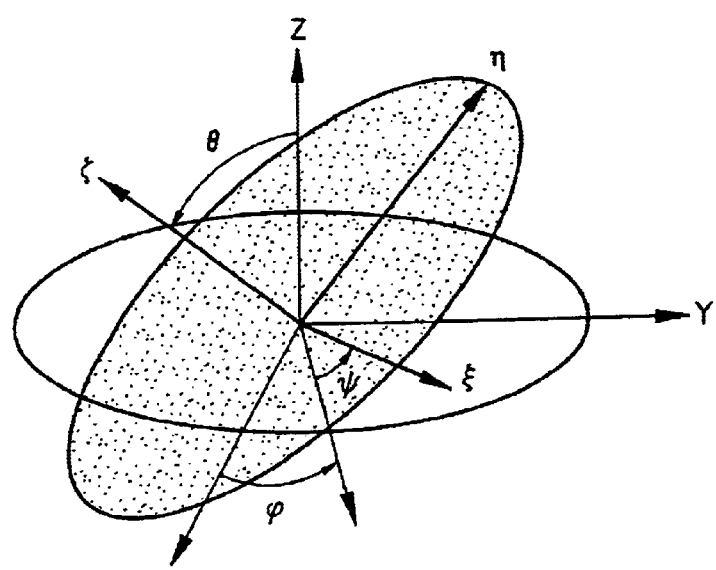
FIG. 3b shows the Euler angles THETA ($\theta$), PHI ($\phi$) and PSI ($\psi$).

For convenient reference, FIG. 3b is included to show the Euler angles, THETA (θ), PHI (φ) and PSI (ψ). Euler angles describe the orientation of an optical axis of a material system with respect to the measurement geometry frame of reference. The PHI (φ) Euler angle is that rotation angle around the normal to said optically thick material system alignment surface necessary to align the optical axis projection in the alignment surface to the measurement frame of reference. The THETA (θ) Euler angle is the angle of the optical axis in the resulting new coordinate system rotated around the resulting new "x"-axis direction; and the PSI (ψ) Euler angle is the angle of the optical axis in this latest resulting new coordinate system rotated around its new "z"-axis.

In experimental ellipsometric work performed to demonstrate practice of the present invention methodology, rectangular shaped bulk $TiO_2$ optically thick material systems oriented (100), (110) and (111), were investigated with electromagnetic radiation in the mid-IR range, (ie. wavelengths of between 5 and 40 microns). For the (100) and (110) orientations the "c" axis, (which is the optical axis), is parallel to the surface probed by the spectroscopic electromagnetic beam, and for the (111) orientation, the "c" axis is neither parallel or perpendicular to the surface probed by the spectroscopic electromagnetic beam.

Figure 5B:
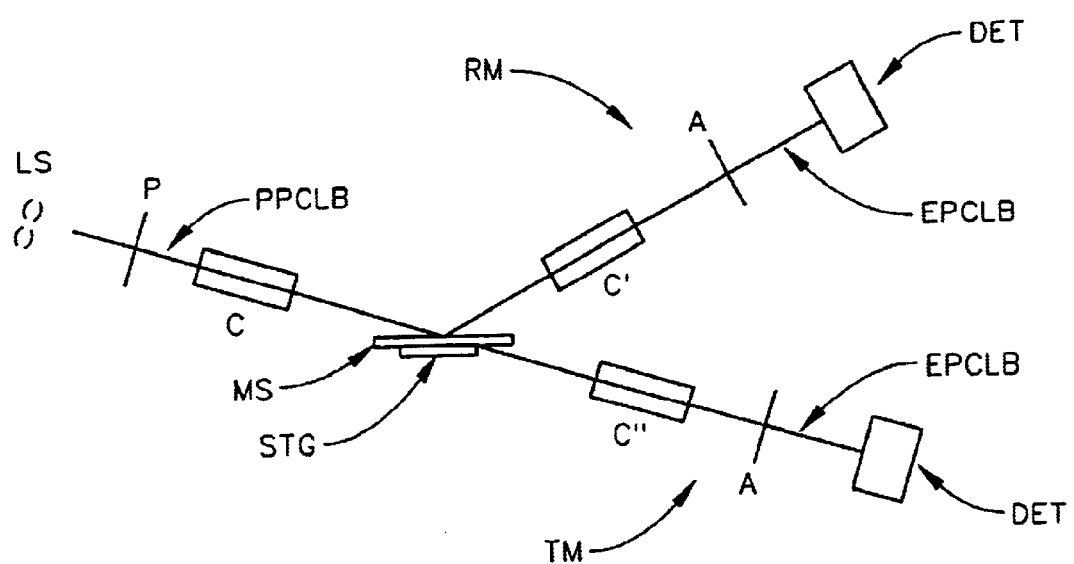
FIG. 5b shows the basic components of an ellipsometer system.

FIG. 5b shows the basic components of an ellipsometer system. A source of electromagnetic radiation (LS) is shown sequentially followed by a Polarizer (P), and optionally a Compensator (C). Also shown are a stage (STG) for supporting a Material System (MS), and both reflective (RM) and transmission (TM) mode Detector Systems (DET), which are preceded by an optional Compensator (C') (C''), and a Polarizer (P). In use a beam (PPCLB) of polychromatic electromagnetic radiation is caused to exit said source of electromagnetic radiation (LS), have imposed upon it a state of polarization, interact with the optically thick material system (MS), then be detected. Change in polarization state in said beam (PPCLB) of polychromatic electromagnetic radiation in becoming (EPCLB), is determinative of Material System characteristics.

FIG. 5a shows an optically thick material system and a beam of electromagnetic radiation oriented in a plane which directs it along the x-axis direction of a rectangular bulk $TiO_2$. For (110) and (100) orientations three orientations of said plane of incidence were utilized during data acquisition:

1. "x-z" plane of incidence positioned along the rectangular $TiO_2$ optically thick material system length (x) direction and perpendicular to the (y) direction;
2. "x-z" plane of incidence positioned along the rectangular $TiO_2$ optically thick material system width (y) direction and perpendicular to the (x) direction;
3. "x-z" plane of incidence positioned rotated between the rectangular $TiO_2$ optically thick material system length (x) and width (y) directions, When investigating the (110) orientation optically thick material system, when electromagnetic beam plane of incidence orientations #1 and #2 were utilized to place the plane of incidence along the optic axis and perpendicular thereto, no conversion between p and s polarizations occur. As a result measurement of the diagonal terms of a reflection Jones matrix using standard ellipsometric measurement was sufficient. Respective ellipsometric PSI and DELTA Spectra, (where the angle of incidence of the electromagnetic beam was 72 degrees), for the orientation #1 are shown in FIGS. 6a1 & 6a2, and for orientation #2 are shown in FIGS. 6b1 & 6b2. When orientation #3 was utilized anisotropic ellipsometric PSI and DELTA data were acquired and are shown in FIGS. 6c1 and 6c2. Date acquired and demonstrated in FIGS. 6a1–6c2 were simultaneously applied in a wavelength by wavelength regression fit to provide the real and imaginary sc and pc dielectric function values. Determined complex dielectric components ($\epsilon_2$) and ($\epsilon_1$) for sc are shown in FIGS. 6d1 & 6d2, and complex dielectric components ($\epsilon_2$) and ($\epsilon_1$) for pc are shown in FIGS. 6e1 & 6e2. Said results were found to be Kramers-Kroenig consistent where values for "offset", Ec and A, (see Kramers-Kroenig equation in the Background Section), were evaluated to be:

| Best-fit parameters for Kramers-Kronig conversion of $\epsilon_2$ to $\epsilon_1$ for (110) sample. | | |
|---|---|---|
| Parameters for K-K fit | $\epsilon_{1-sc}$ | $\epsilon_{1-pc}$ |
| offset. | 5.72 ± 0.02 | 5.47 ± 0.02 |
| $E_c$ | 0.0226 ± 0.0001 | 0.0226 ± 1 × 10$^{-4}$ |
| A | 2.403 ± 0.03 | 3.83 ± 0.03 |

When investigating the (100) orientation optically thick material system, when orientation #3 was utilized anisotropic ellipsometric PSI and DELTA data were acquired and are shown in FIGS. 7a1 and 7a2. As in the (110) case, in all #3, #1 and #2 orientations, the angle of incidence of the electromagnetic beam was 72 degrees. When electromagnetic beam plane of incidence orientations #1 and #2 were utilized to place the plane of incidence along the optic axis and perpendicular thereto, no conversion between p and s polarizations occur. As a result measurement of the diagonal terms of a reflection Jones matrix using standard ellipsometric measurement was sufficient. Respective ellipsometric PSI and DELTA Spectra, for the orientation #1 are shown in FIGS. 7b1 & 7b2, and for orientation #2 are shown in FIGS. 7c1 & 7c2. The slight conversion between p and s was due to slight misalignment of the "c" axis in the (x-y) plane. Date acquired and demonstrated in FIGS. 7a1–7c2 were simultaneously applied in a wavelength by wavelength regression fit to provide the real and imaginary sc and pc dielectric function values. Determined complex dielectric components ($\epsilon_1$) and ($\epsilon_2$) for sc are shown in FIGS. 7d1 & 7d2, and complex dielectric components ($\epsilon_1$) and ($\epsilon_2$) for pc are shown in FIGS. 7e1 & 7e2. Said results were found to be Kramers-Kroenig consistent where values for "offset", Ec and A, (see Kramers-Kroenig equation in the Background Section), were evaluated to be:

| Best-fit parameters for Kramers-Kronig conversion of $\epsilon_2$ to $\epsilon_1$ for (100) sample. | | |
|---|---|---|
| Parameters for sample (100) K-K fit | $\epsilon_{1-sc}$ | $\epsilon_{1-pc}$ |
| offset. | 6.93 ± 0.03 | 5.89 ± 0.01 |
| $E_c$ | 0.0234 ± 0.0001 | 0.0232 ± 1 × 10$^{-4}$ |
| A | 3.73 ± 0.03 | 2.41 ± 0.01 |

In the case of the (111) sample, the "c" axis is not parallel to the (x-y) plane (ie. in-plane), or perpendicular thereto. Measurements were obtained with the plane of incidence oriented at four different locations, (eg. at −109, −18.8, −66.1 and 21.54 degrees rotation of the optically thick material system around a perpendicular to an alignment surface thereof). Measurements at three of the orientations were obtained using 72 degrees angle of incidence, and at one orientation, (ie. the 21.54 degrees rotation), data was obtained using 30 and 55 degrees angles of incidence. FIGS. 8a1, 8b1, 8c1, and 8d1, show corresponding ellipsometric PSI results, and FIGS. 8a2, 8d2, 8c2 and 8d2 show corresponding ellipsometric DELTA values. Date acquired and demonstrated in FIGS. 8a1–8d2 were simultaneously applied in a wavelength by wavelength regression fit to provide the real and imaginary sc and pc dielectric function values. Determined complex dielectric components ($\in_2$) and ($\in_1$) for sc are shown in FIGS. 8e1 & 8e2, and complex dielectric components ($\in_2$) and ($\in_1$) for pc are shown in FIGS. 8f1 & 8f2. Said results were found to be Kramers-Kroenig consistent where values for "offset", Ec and A, (see Kramers-Kroenig equation in the Background Section), were evaluated to be:

| Best-fit parameters for Kramers-Kronig conversion of $\epsilon_2$ to $\epsilon_1$ for (111) sample. | | |
|---|---|---|
| Parameters for sample (111) K-K fit | $\epsilon_{1\text{-sc}}$ | $\epsilon_{1\text{-pc}}$ |
| offset. | 5.53 ± 0.04 | 6.7 ± 0.2 |
| $E_c$ | 0.0289 ± 0.0001 | 0.0244 ± 0.0007 |
| A | 2.50 ± 0.02 | 3.2 ± 0.2 |

Figure 9A:
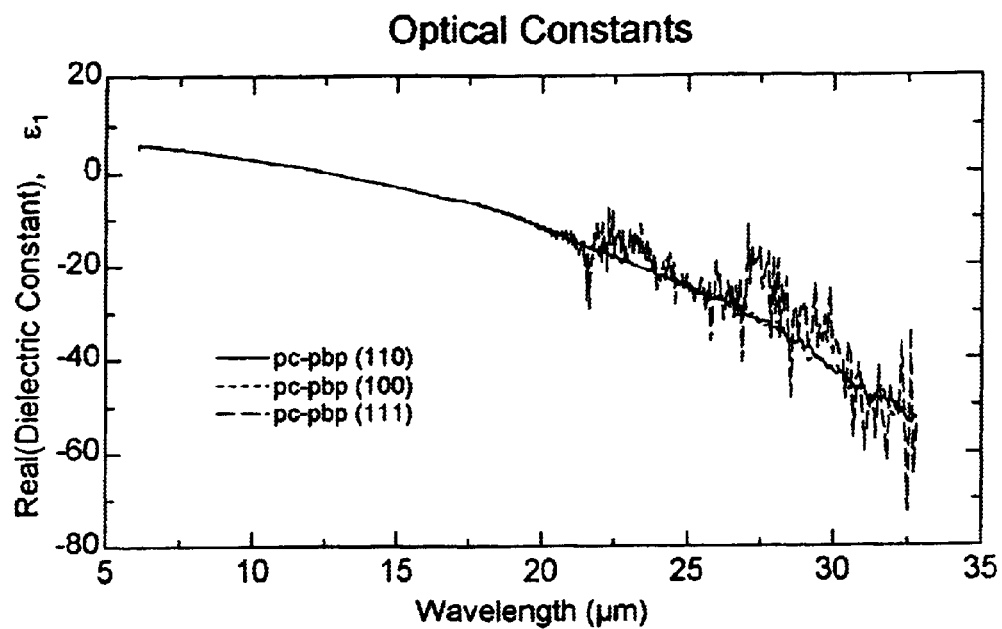
FIGS. 9a and 9b show real and imaginary pc dielectric constants for all three $TiO_2$ optically thick material system orientations (110), (100) and (111).
Figure 9B:
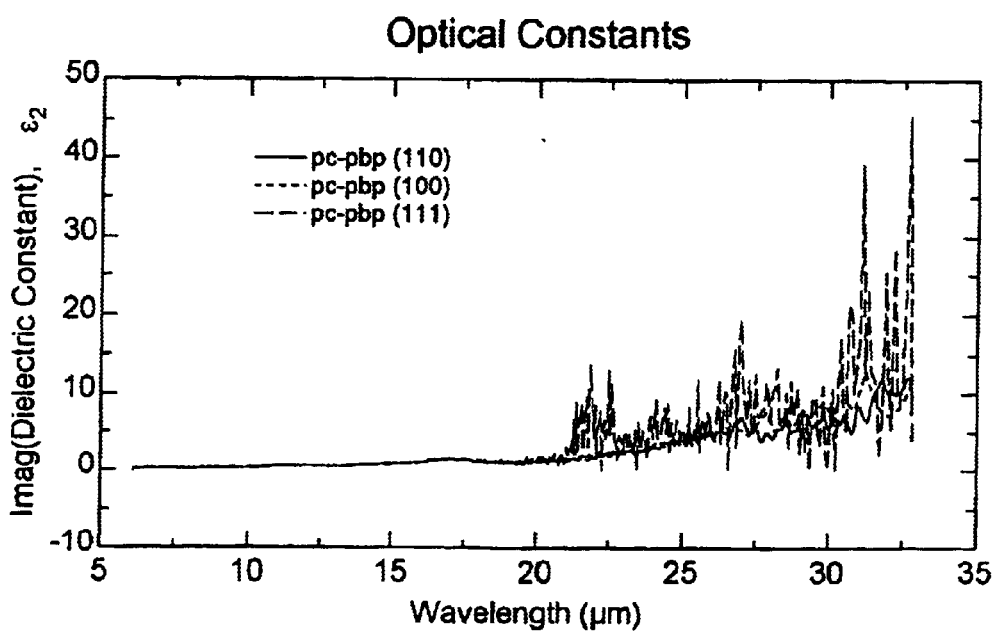
Figure 10A:
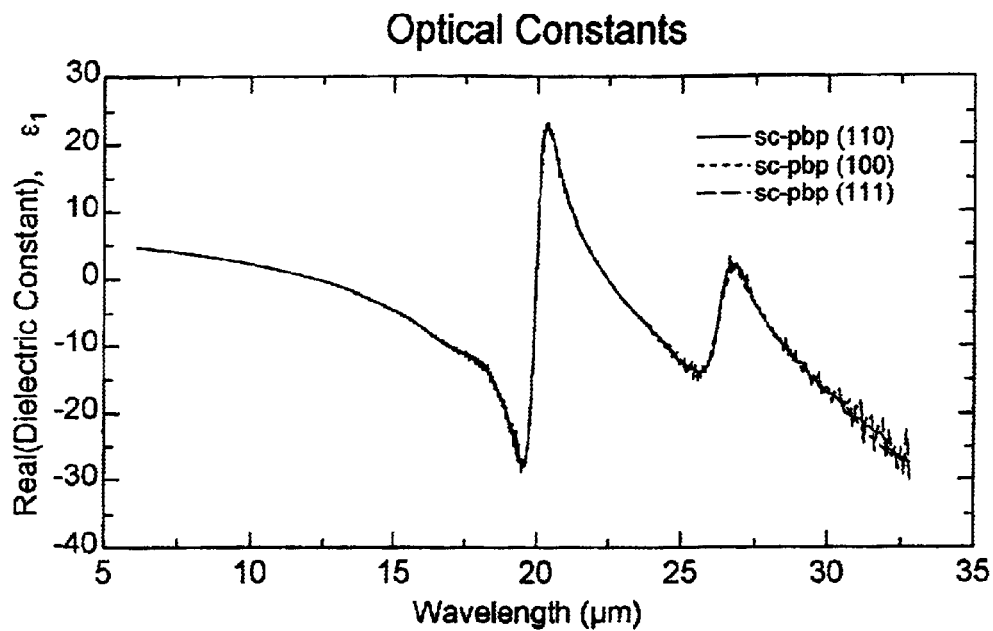
FIGS. 10a and 10b show real and imaginary sc dielectric constants for all three $TiO_2$ optically thick material system orientations (110), (100) and (111).
Figure 10B:
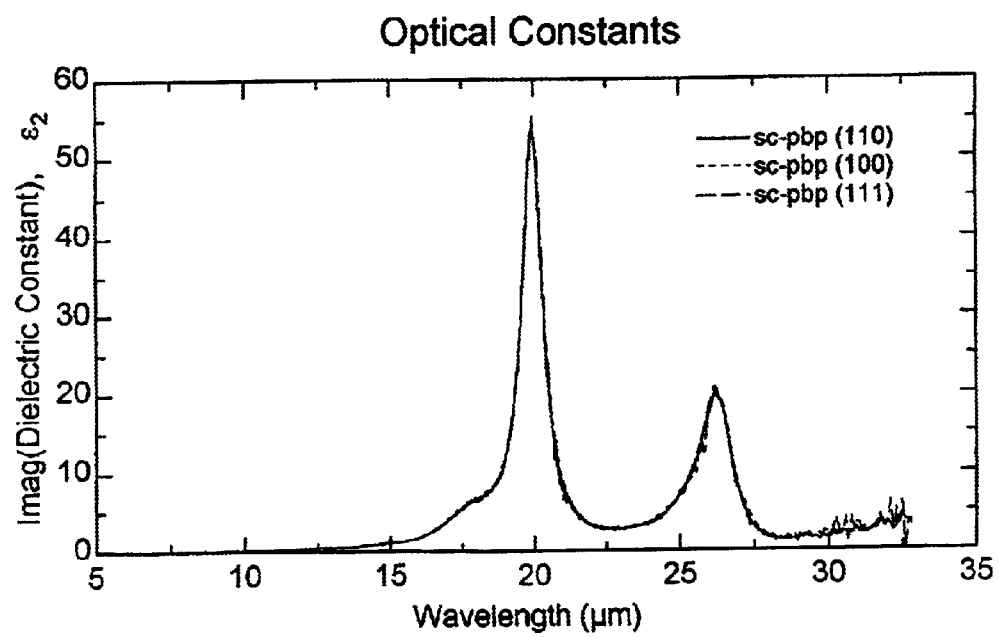

FIGS. 9a and 9b show real and imaginary pc dielectric constants for all three $TiO_2$ optically thick material system orientations (110), (100) and (111). Note that the fit is very good in all said cases, but the noise is present beyond 20 microns for the (111) case FIGS. 10a and 10b show real and imaginary sc dielectric constants for all three $TiO_2$ optically thick material system orientations (110), (100) and (111).

In all cases demonstrated, experimental data was fit using a wavelength by wavelength approach.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

I claim:

1. A method of evaluating mathematical model parameters describing Euler angles and directions, and magnitudes of real and imaginary components, of orthogonally related Kramers-Kroenig consistent complex dielectric functions or refractive indicies in an optically thick material system wherein a beam of electromagnetic radiation reflected from an alignment surface thereof is comprised primarily of components reflecting directly from said alignment surface, said optically thick material system presenting with an optical axis oriented in a selection from the group consisting of:

in-plane; and out-of-plane;

with respect to said alignment surface thereof, said optically thick material system being uniaxial in that corresponding real and corresponding imaginary components of at least two orthogonally related optically thick material system characterizing diagonalized tensor:

$$\overline{\varepsilon}(E) = \begin{bmatrix} \varepsilon_{sc} & 0 & 0 \\ 0 & \varepsilon_{sc} & 0 \\ 0 & 0 & \varepsilon_{pc} \end{bmatrix}$$

complex dielectric functions or refractive indicies identified on said diagonal are of equal magnitude, said method comprising, in any functional order, the steps of:

a) providing an optically thick material system which presents with Kramers-Kroenig consistent complex dielectric functions or refractive indicies and with an optical axis oriented either in-plane or out-of-plane with respect to an alignment surface thereof, said optically thick material system being uniaxial in that corresponding real and corresponding imaginary components of at least two orthogonally related optically thick material system characterizing diagonalized tensor:

$$\overline{\varepsilon}(E) = \begin{bmatrix} \varepsilon_{sc} & 0 & 0 \\ 0 & \varepsilon_{sc} & 0 \\ 0 & 0 & \varepsilon_{pc} \end{bmatrix}$$

complex dielectric functions or refractive indicies are of equal magnitude;

b) placing said optically thick material system into a system for directing at least one spectroscopic polarized electromagnetic beam(s) of radiation onto said alignment surface at at least one angle(s) of incidence removed from a normal to said alignment surface, said system for directing at least one spectroscopic polarized electromagnetic beam(s) of radiation onto said alignment surface at at least one angle(s) of incidence removed from a normal to said alignment surface comprising a reflection detector system;

c) selecting at least one spectroscopic polarized electromagnetic beam(s) of radiation to at least partially comprise wavelengths for which said optically thick material system is non-transparent, and causing said at least one beam(s) of spectroscopic polarized electromagnetic radiation to impinge on said alignment surface of said optically thick material system, at at least one angle(s) of incidence removed from a normal to said alignment surface, in plane(s) of incidence which include the locus of said beam of spectroscopic polarized electromagnetic radiation and said normal to said alignment surface, said at least one beam(s) of spectroscopic polarized electromagnetic radiation being caused to reflect from said alignment surface of said optically thick material system and into said reflection detector system;

d) at said at least one angle(s) of incidence and at at least two rotation angles of said optically thick material system around said normal to the alignment surface thereof, obtaining reflection detector system mediated experimental reflection intensity data as a functions of wavelength and angle of incidence of said at least one beam of spectroscopic polarized electromagnetic radiation onto said optically thick material system alignment surface;

e) simultaneously providing a mathematical model of said optically thick material system which includes as parameters therein at least:

real and imaginary components for each of the orthogonally related, Kramers-Kroenig consistent tensor diagonal complex dielectric functions or refractive indicies;

sufficient rotation about a normal to an alignment surface, and deviation from alignment with said alignment surface angle parameters to define the orientations of the orthogonally related, Kramers-Kroenig consistent tensor diagonal complex dielectric functions or refractive indicies, and orientation of the optical axis, with respect to the alignment surface; and Euler angles relating material system angles to a laboratory frame of reference; and f) via application of a mathematical regression technique, evaluating parameters in said mathematical model to provide a best-fit to acquired experimental data.

2. A method of evaluating mathematical model parameters as in claim 1, in which the step of, at at least two rotation angles of said optically thick material system around said normal to the alignment surface thereof, obtaining experimental reflection intensity data as a functions of wavelength and angle of incidence of said at least one beam of spectroscopic polarized electromagnetic radiation onto said optically thick material system alignment surface, involves obtaining experimental reflection data at at least two angles of incidence.

3. A method of evaluating mathematical model parameters as in claim 1, in which the step of, at at least two rotation angles of said optically thick material system around said normal to the alignment surface thereof, obtaining experimental reflection intensity data as a functions of wavelength and angle of incidence of said at least one beam of spectroscopic polarized electromagnetic radiation onto said optically thick material system alignment surface, involves obtaining experimental reflection data at at least two angles of incidence and at two or more rotation angles of said optically thick material system around said normal to the alignment surface thereof.

4. A method of evaluating mathematical model parameters as in claim 1, in which the step of, at at least two rotation angles of said optically thick material system around said normal to the alignment surface thereof, obtaining experimental reflection intensity data as a functions of wavelength and angle of incidence of said at least one beam of spectroscopic polarized electromagnetic radiation onto said optically thick material system alignment surface, involves obtaining experimental reflection data at two rotation angles of said optically thick material system around said normal to the alignment surface thereof, said two rotation angles being appropriate to sequentially align a plane of incidence of said at least one spectroscopic polarized electromagnetic beam of radiation along the direction of an in-plane projection of two of the orthogonally related complex dielectric functions or refractive indicies which have equal magnitude corresponding real and equal magnitude corresponding imaginary components.

5. A method of evaluating mathematical model parameters as in claim 1, in which the step of, at at least two rotation angles of said optically thick material system around said normal to the alignment surface thereof, obtaining experimental reflection intensity data as a functions of wavelength and angle of incidence of said at least one beam of spectroscopic polarized electromagnetic radiation onto said optically thick material system alignment surface, involves obtaining experimental reflection data at two rotation angles of said optically thick material system around said normal to the alignment surface thereof, said two rotation angles being appropriate to sequentially align a plane of incidence of said at least one spectroscopic polarized electromagnetic beam of radiation along the direction of an in-plane projection of one of said two orthogonally related dielectric functions or refractive indicies which have equal magnitude corresponding real and equal magnitude corresponding imaginary components, and further involves obtaining experimental reflection data with said plane of incidence of said at least one beam of spectroscopic polarized electromagnetic radiation oriented along a direction rotationally between the directions of said in-plane projections of said two orthogonally related complex dielectric functions or refractive indicies which have equal magnitude corresponding real and equal magnitude corresponding imaginary components.

6. A method of evaluating mathematical model parameters as in claim 4, in which the step of, at at least two rotation angles of said optically thick material system around said normal to the alignment surface thereof, obtaining experimental reflection intensity data as a functions of wavelength and angle of incidence of said at least one beam of spectroscopic polarized electromagnetic radiation onto said optically thick material system alignment surface, involves obtaining experimental reflection data at at least two angles of incidence at each rotation angle.

7. A method of evaluating mathematical model parameters as in claim 5, in which the step of, at at least two rotation angles of said optically thick material system around said normal to the alignment surface thereof, obtaining experimental reflection intensity data as a functions of wavelength and angle of incidence of said at least one beam of spectroscopic polarized electromagnetic radiation onto said optically thick material system alignment surface, involves obtaining experimental reflection data at at least two angles of incidence at each rotation angle.

8. A method of evaluating mathematical model parameters as in claim 1, in which a optically thick material system is provided that has the optical axis oriented out-of-plane with respect to said alignment surface, and in which the steps of obtaining experimental reflection data at at least one angle(s) of incidence of said at least one beam of spectroscopic electromagnetic radiation removed from a normal to said alignment surface, involves causing at said least one beam of spectroscopic polarized electromagnetic radiation to sequentially impinge on said alignment surface of said optically thick material system along two or more angles of incidence removed from a normal to said alignment surface are utilized.

9. A method of evaluating mathematical model parameters as in claim 1, in which a optically thick material system is provided that has the optical axis oriented in-plane with respect to said alignment surface, and in which the steps of obtaining experimental reflection data at at least one angle(s) of incidence of said at least one beam of spectroscopic electromagnetic radiation removed from a normal to said alignment surface, involves causing at said least one beam of spectroscopic polarized electromagnetic radiation to sequentially impinge on said alignment surface of said optically thick material system along two or more angles of incidence removed from a normal to said alignment surface are utilized.

10. A method of evaluating mathematical model parameters as in claim 1, wherein said mathematical regression technique involves reduction of square-error.

11. A method of evaluating mathematical model parameters as in claim 1, which further comprises providing a transmission detector and obtaining transmission data at at least one angle(s) of incidence of said at least one beam of spectroscopic electromagnetic radiation removed from a normal to said alignment surface.

12. A method of evaluating mathematical model parameters describing directions, and magnitudes of real and imaginary components, of orthogonally related Kramers-Kroenig consistent complex dielectric functions or refractive indicies in an optically thick material system wherein a beam of electromagnetic radiation reflected from an alignment surface thereof is comprised primarily of components reflecting directly from said alignment surface, said optically thick material system presenting with an optical axis oriented in a selection from the group consisting of:

in-plane; and out-of-plane;

with respect to said alignment surface thereof, said optically thick material system being uniaxial in that corresponding real and corresponding imaginary components of at least two orthogonally related optically thick material system characterizing diagonalized tensor:

$$\overline{\varepsilon}(E) = \begin{bmatrix} \varepsilon_{sc} & 0 & 0 \\ 0 & \varepsilon_{sc} & 0 \\ 0 & 0 & \varepsilon_{pc} \end{bmatrix}$$

complex dielectric functions or refractive indicies identified on said diagonal are of equal magnitude, said method comprising, in any functional order, the steps of:

a) providing at least two optically thick material systems which each present with Kramers-Kroenig consistent complex dielectric functions or refractive indicies and with an optical axis oriented either in-plane or out-of-plane with respect to an alignment surface thereof, each said optically thick material system being at least uniaxial in that corresponding real and corresponding imaginary components of at least two orthogonally related optically thick material system characterizing diagonalized tensor:

$$\overline{\varepsilon}(E) = \begin{bmatrix} \varepsilon_{sc} & 0 & 0 \\ 0 & \varepsilon_{sc} & 0 \\ 0 & 0 & \varepsilon_{pc} \end{bmatrix}$$

complex dielectric functions or refractive indicies are of equal magnitude;

said method further comprising, for each said optically thick material system:

b) placing said optically thick material system into a system for directing at least one spectroscopic polarized electromagnetic beam(s) of radiation onto said alignment surface at at least one angle(s) of incidence removed from a normal to said alignment surface, said system for directing at least one spectroscopic polarized electromagnetic beam(s) of radiation onto said alignment surface at at least one angle(s) of incidence removed from a normal to said alignment surface comprising a reflection detector system;

c) selecting at least one spectroscopic polarized electromagnetic beam(s) of radiation to at least partially comprise wavelengths for which said optically thick material system is non-transparent, and causing said at least one beam(s) of spectroscopic polarized electromagnetic radiation to impinge on said alignment surface of said optically thick material system, at at least one angle(s) of incidence removed from a normal to said alignment surface, in plane(s) of incidence which include the locus of said beam of spectroscopic polarized electromagnetic radiation and said normal to said alignment surface, said at least one beam(s) of spectroscopic polarized electromagnetic radiation being caused to reflect from said alignment surface of said optically thick material system and into said reflection detector system;

d) at said at least one angle(s) of incidence and at at least two rotation angles of said optically thick material system around said normal to the alignment surface thereof, obtaining reflection detector system mediated experimental reflection intensity data as a functions of wavelength and angle of incidence of said at least one beam of spectroscopic polarized electromagnetic radiation onto said optically thick material system alignment surface;

e) simultaneously providing a mathematical model of said optically thick material system which includes as parameters therein at least:

real and imaginary components for each of the orthogonally related, Kramers-Kroenig consistent tensor diagonal complex dielectric functions or refractive indicies;

sufficient rotation about a normal to an alignment surface, and deviation from alignment with said alignment surface angle parameters to define the orientations of the orthogonally related, Kramers-Kroenig consistent tensor diagonal complex dielectric functions or refractive indicies, and orientation of the optical axis, with respect to the alignment surface; and Euler angles relating material system angles to a laboratory frame of reference; and and wherein said method further comprises:

f) via application of a mathematical regression technique, simultaneously evaluating parameters in said mathematical models for each of the investigated optically thick material systems to provide a best-fit to acquired experimental data.

13. A method of evaluating mathematical model parameters describing directions and magnitudes of real and imaginary components of orthogonally related Kramers-Kroenig consistent complex dielectric functions or refractive indicies in optically thick material system wherein a beam of electromagnetic radiation reflected from an alignment surface thereof is comprised primarily of components reflecting directly from said alignment surface, said optically thick material system presenting with an optical axis oriented in a selection from the group consisting of:

in-plane; and out-of-plane;

with respect to said alignment surface thereof, said optically thick material system being biaxial in that corresponding real and corresponding imaginary components of said orthogonally related optically thick material system characterizing diagonalized tensor:

$$\overline{\varepsilon}(E) = \begin{bmatrix} \varepsilon_{sc} & 0 & 0 \\ 0 & \varepsilon_{sc} & 0 \\ 0 & 0 & \varepsilon_{pc} \end{bmatrix}$$

complex dielectric functions or refractive indicies identified on said diagonal are unequal in magnitude;
said method comprising, in any functional order, the steps of:
   a) providing an optically thick material system which presents with Kramers-Kroenig consistent complex dielectric functions or refractive indicies and with an optical axis oriented either in-plane or out-of-plane with respect to an alignment surface thereof, said optically thick material system being biaxial in that corresponding real and corresponding imaginary components of said orthogonally related optically thick material system characterizing diagonalized tensor:

$$\overline{\varepsilon}(E) = \begin{bmatrix} \varepsilon_{sc} & 0 & 0 \\ 0 & \varepsilon_{sc} & 0 \\ 0 & 0 & \varepsilon_{pc} \end{bmatrix}$$

complex dielectric functions or refractive indicies are unequal in magnitude;
   b) placing said optically thick material system into a system for directing at least one spectroscopic polarized electromagnetic beam(s) of radiation onto said alignment surface at at least one angle(s) of incidence removed from a normal to said alignment surface, said system for directing at least one spectroscopic polarized electromagnetic beam(s) of radiation onto said alignment surface at at least one angle(s) of incidence removed from a normal to said alignment surface comprising a reflection detector system;
   c) selecting at least one spectroscopic polarized electromagnetic beam(s) of radiation to at least partially comprise wavelengths for which said optically thick material system is non-transparent, and causing said at least one beam(s) of spectroscopic polarized electromagnetic radiation to impinge on said alignment surface of said optically thick material system, at at least one angle(s) of incidence removed from a normal to said alignment surface, in plane(s) of incidence which include the locus of said beam of spectroscopic polarized electromagnetic radiation and said normal to said alignment surface, said at least one beam(s) of spectroscopic polarized electromagnetic radiation being caused to reflect from said alignment surface of said optically thick material system and into said reflection detector system;
   d) at said at least one angle of incidence and at more than two rotation angles of said optically thick material system around said normal to the alignment surface thereof, obtaining reflection detector system mediated experimental reflection intensity data as a functions of wavelength and angle of incidence of said at least one beam of spectroscopic polarized electromagnetic radiation onto said optically thick material system alignment surface;
   e) simultaneously providing a mathematical model of said optically thick material system which includes as parameters therein at least:

real and imaginary components for each of the orthogonally related, Kramers-Kroenig consistent tensor diagonal complex dielectric functions refractive indicies;
sufficient rotation about a normal to an alignment surface, and deviation from alignment with said alignment surface angle parameters to define the orientations of the orthogonally related, Kramers-Kroenig consistent tensor diagonal complex dielectric functions or refractive indicies, and orientation of the optical axis, with respect to the alignment surface; and
Euler angles relating material system angles to a laboratory frame of reference; and
   f) via application of a mathematical regression technique, evaluating parameters in said mathematical model to provide a best-fit to acquired experimental data.

14. A method of evaluating mathematical model parameters describing directions and magnitudes of real and imaginary components of orthogonally related Kramers-Kroenig consistent complex dielectric functions or refractive indicies in optically thick material system wherein a beam of electromagnetic radiation reflected from an alignment surface thereof is comprised primarily of components reflecting directly from said alignment surface, said optically thick material system presenting with an optical axis oriented in a selection from the group consisting of:
   in-plane; and
   out-of-plane;
with respect to said alignment surface thereof, said optically thick material system being biaxial in that corresponding real and corresponding imaginary components of said orthogonally related optically thick material system characterizing diagonalized tensor:

$$\overline{\varepsilon}(E) = \begin{bmatrix} \varepsilon_{sc} & 0 & 0 \\ 0 & \varepsilon_{sc} & 0 \\ 0 & 0 & \varepsilon_{pc} \end{bmatrix}$$

complex dielectric functions or refractive indicies identified on said diagonal are unequal in magnitude;
said method comprising, in any functional order, the steps of:
   a) providing an optically thick material system which presents with Kramers-Kroenig consistent complex dielectric functions or refractive indicies and with an optical axis oriented either in-plane or out-of-plane with respect to an alignment surface thereof, said optically thick material system being biaxial in that corresponding real and corresponding imaginary components of said orthogonally related optically thick material system characterizing diagonalized tensor:

$$\overline{\varepsilon}(E) = \begin{bmatrix} \varepsilon_{sc} & 0 & 0 \\ 0 & \varepsilon_{sc} & 0 \\ 0 & 0 & \varepsilon_{pc} \end{bmatrix}$$

complex dielectric functions or refractive indicies are unequal in magnitude;
   b) placing said optically thick material system into a system for directing at least one spectroscopic polarized electromagnetic beam(s) of radiation onto said alignment surface at at least one angle(s) of incidence removed from a normal to said alignment surface, said system for directing at least one spectroscopic polarized electromagnetic beam(s) of radiation onto said alignment surface at least one angle(s) of incidence removed from a normal to said alignment surface comprising a reflection detector system;

c) selecting at least one spectroscopic polarized electromagnetic beam(s) of radiation to at least partially comprise wavelengths for which said optically thick material system is non-transparent, and causing said at least one beam(s) of spectroscopic polarized electromagnetic radiation to impinge on said alignment surface of said optically thick material system, at at least one angle(s) of incidence removed from a normal to said alignment surface, in plane(s) of incidence which include the locus of said beam of spectroscopic polarized electromagnetic radiation and said normal to said alignment surface, said at least one beam(s) of spectroscopic polarized electromagnetic radiation being caused to reflect from said alignment surface of said optically thick material system and into said reflection detector system;

d) at at least two angles of incidence and at at least two rotation angles of said optically thick material system around said normal to the alignment surface thereof, obtaining reflection detector system mediated experimental reflection intensity data as a functions of wavelength and angle of incidence of said at least one beam of spectroscopic polarized electromagnetic radiation onto said optically thick material system alignment surface;

e) simultaneously providing a mathematical model of said optically thick material system which includes as parameters therein at least:

real and imaginary components for each of the orthogonally related, Kramers-Kroenig consistent tensor diagonal complex dielectric functions or refractive indicies;

sufficient rotation about a normal to an alignment surface, and deviation from alignment with said alignment surface angle parameters to define the orientations of the orthogonally related, Kramers-Kroenig consistent tensor diagonal complex dielectric functions or refractive indicies, and orientation of the optical axis, with respect to the alignment surface; and Euler angles relating material system angles to a laboratory frame of reference; and f) via application of a mathematical regression technique, evaluating parameters in said mathematical model to provide a best-fit to acquired experimental data.

15. A method of evaluating mathematical model parameters as in claim 1, in which the wavelengths selected, for which said optically thick material system is non-transparent, are in the infrared range of 5 to 40 microns.

16. A method of evaluating mathematical model parameters as in claim 12, in which the wavelengths selected, for which said optically thick material system is non-transparent, are in the infrared range of 5 to 40 microns.

17. A method of evaluating mathematical model parameters as in claim 13, in which the wavelengths selected, for which said optically thick material system is non-transparent, are in the infrared range of 5 to 40 microns.

18. A method of evaluating mathematical model parameters as in claim 14, in which the wavelengths selected, for which said optically thick material system is non-transparent, are in the infrared range of 5 to 40 microns.

19. A method of evaluating mathematical model parameters describing Euler angles and directions, and magnitudes of real and imaginary components, of orthogonally related Kramers-Kroenig consistent complex dielectric functions or refractive indicies in an optically thick material system wherein a beam of electromagnetic radiation reflected from an alignment surface thereof is comprised primarily of components reflecting directly from said alignment surface, said optically thick material system presenting with an optical axis oriented in a selection from the group consisting of:

in-plane; and out-of-plane;

with respect to said alignment surface thereof;

said method comprising, in any functional order, the steps of:

a) providing an optically thick material system which presents with Kramers-Kroenig consistent complex dielectric functions or refractive indicies, and with an optical axis oriented either in-plane or out-of-plane with respect to an alignment surface thereof;

b) placing said optically thick material system into a system for directing at least one spectroscopic polarized electromagnetic beam(s) of radiation onto said alignment surface at at least one angle(s) of incidence removed from a normal to said alignment surface, said system for directing at least one spectroscopic polarized electromagnetic beam(s) of radiation onto said alignment surface at at least one angle(s) of incidence removed from a normal to said alignment surface comprising a reflection detector system;

c) selecting at least one spectroscopic polarized electromagnetic beam(s) of radiation to at least partially comprise wavelengths for which said optically thick material system is non-transparent, and causing said at least one beam(s) of spectroscopic polarized electromagnetic radiation to impinge on said alignment surface of said optically thick material system, at at least one angle(s) of incidence removed from a normal to said alignment surface, in plane(s) of incidence which include the locus of said beam of spectroscopic polarized electromagnetic radiation and said normal to said alignment surface, said at least one beam(s) of spectroscopic polarized electromagnetic radiation being caused to reflect from said alignment surface of said optically thick material system and into said reflection detector system;

d) at said at least one angle(s) of incidence and at at least two rotation angles of said optically thick material system around said normal to the alignment surface thereof, obtaining reflection detector system mediated experimental reflection intensity data as a functions of wavelength and angle of incidence of said at least one beam of spectroscopic polarized electromagnetic radiation onto said optically thick material system alignment surface;

e) simultaneously providing a mathematical model of said optically thick material system which includes as parameters therein at least:

real and imaginary components for each of the orthogonally related, Kramers-Kroenig consistent tensor diagonal complex dielectric functions or refractive indicies;

sufficient rotation about a normal to an alignment surface, and deviation from alignment with said alignment surface angle parameters to define the orientations of the orthogonally related, Kramers-Kroenig consistent tensor diagonal complex dielectric functions or refractive indicies, and orientation of the optical axis, with respect to the alignment surface; and Euler angles relating material system angles to a laboratory frame of reference; and f) via application of a mathematical regression technique, evaluating parameters in said mathematical model to provide a best-fit to acquired experimental data.

20. A method of evaluating mathematical model parameters as in claim 19, in which the wavelengths selected, for which said optically thick material system is non-transparent, are in the infrared range of 5 to 40 microns.

21. A method of evaluating mathematical model parameters describing Euler angles and directions, and magnitudes of real and imaginary components, of orthogonally related Kramers-Kroenig consistent complex dielectric functions or refractive indicies in an optically thick material system wherein a beam of electromagnetic radiation reflected from an alignment surface thereof is comprised primarily of components reflecting directly from said alignment surface, said optically thick material system presenting with an optical axis oriented in a selection from the group consisting of:

in-plane; and out-of-plane;

with respect to said alignment surface thereof, said optically thick material system being uniaxial in that corresponding real and corresponding imaginary components of at least two orthogonally related optically thick material system characterizing diagonalized tensor:

$$\overline{\varepsilon}(E) = \begin{bmatrix} \varepsilon_{sc} & 0 & 0 \\ 0 & \varepsilon_{sc} & 0 \\ 0 & 0 & \varepsilon_{pc} \end{bmatrix}$$

complex dielectric functions or refractive indicies identified on said diagonal are of equal magnitude, said method comprising, in any functional order, the steps of:

a) providing an optically thick material system which presents with Kramers-Kroenig consistent complex dielectric functions or refractive indicies and with an optical axis oriented either in-plane or out-of-plane with respect to an alignment surface thereof, said optically thick material system being uniaxial in that corresponding real and corresponding imaginary components of at least two orthogonally related optically thick material system characterizing diagonalized tensor:

$$\overline{\varepsilon}(E) = \begin{bmatrix} \varepsilon_{sc} & 0 & 0 \\ 0 & \varepsilon_{sc} & 0 \\ 0 & 0 & \varepsilon_{pc} \end{bmatrix}$$

complex dielectric functions or refractive indicies are of equal magnitude;

b) placing said optically thick material system into a system for directing at least one spectroscopic polarized electromagnetic beam(s) of radiation onto said alignment surface at at least one angle(s) of incidence removed from a normal to said alignment surface, said system for directing at least one spectroscopic polarized electromagnetic beam(s) of radiation onto said alignment surface at at least one angle(s) of incidence removed from a normal to said alignment surface comprising a reflection detector system;

c) selecting at least one spectroscopic polarized electromagnetic beam(s) of radiation to at least partially comprise wavelengths for which said optically thick material system is non-transparent, and causing said at least one beam(s) of spectroscopic polarized electromagnetic radiation to impinge on said alignment surface of said optically thick material system, at at least one angle(s) of incidence removed from a normal to said alignment surface, in plane(s) of incidence which include the locus of said beam of spectroscopic polarized electromagnetic radiation and said normal to said alignment surface, said at least one beam(s) of spectroscopic polarized electromagnetic radiation being caused to reflect from said alignment surface of said optically thick material system and into said reflection detector system;

d) at said at least one angle(s) of incidence and at one rotation angle of said optically thick material system around said normal to the alignment surface thereof, obtaining reflection detector system mediated experimental reflection intensity data as a functions of wavelength and angle of incidence of said at least one beam of spectroscopic polarized electromagnetic radiation onto said optically thick material system alignment surface;

e) from the data obtained in step d., determining Jones Matrix:

$$\begin{bmatrix} Epo \\ Eso \end{bmatrix} = \begin{bmatrix} Tpp & Tsp \\ Tps & Tss \end{bmatrix} \begin{bmatrix} Epi \\ Esi \end{bmatrix}$$

components and if the off-diagonal components are essentially zero, rotate the optically thick material system about a perpendicular to the alignment surface thereof, and proceeding to step f and if not proceeding directly to step g;

f) at said at least one angle(s) of incidence and at one rotation angle of said optically thick material system around said normal to the alignment surface thereof, obtaining reflection detector system mediated experimental reflection intensity data as a functions of wavelength and angle of incidence of said at least one beam of spectroscopic polarized electromagnetic radiation onto said optically thick material system alignment surface;

g) simultaneously providing a mathematical model of said optically thick material system which includes as parameters therein at least:

real and imaginary components for each of the orthogonally related, Kramers-Kroenig consistent tensor diagonal complex dielectric functions or refractive indicies;

sufficient rotation about a normal to an alignment surface, and deviation from alignment with said alignment surface angle parameters to define the orientations of the orthogonally related, Kramers-Kroenig consistent tensor diagonal complex dielectric functions or refractive indicies, and orientation of the optical axis, with respect to the alignment surface; and Euler angles relating material system angles to a laboratory frame of reference; and h) via application of a mathematical regression technique, evaluating parameters in said mathematical model to provide a best-fit to acquired experimental data.

22. A method of evaluating mathematical model parameters as in claim 1 wherein, after providing optically thick material system, a screening step of evaluating of components of selection from the group consisting of:

a material system representing Jones Matrix; and a material system representing Mueller Matrix;

is practiced, followed by practicing a selection from the group consisting of:

continuing if said off-Diagonal terms are not essentially zero (0.0); and if said off-Diagonal terms are essentially zero (0.0), first rotating the material system so that said Off-Diagonal terms become other than essentially zero (0.0).

23. A method of evaluating mathematical model parameters as in claim 11 wherein, after providing said at least two optically thick material systems, a screening step of evaluating of components of a selection from the group consisting of:

a material system representing Jones Matrix; and a material system representing Mueller Matrix;

is practiced, followed by practicing a selection from the group consisting of:

continuing if said off-Diagonal terms are not essentially zero (0.0); and if said off-Diagonal terms are essentially zero (0.0), first rotating the material system so that said Off-Diagonal terms become other than essentially zero (0.0).

24. A method of evaluating mathematical model parameters as in claim 13 wherein, after providing optically thick material system, a screening step of evaluating of components of a selection from the group consisting of:

a material system representing Jones Matrix; and a material system representing Mueller Matrix;

is practiced, followed by practicing a selection from the group consisting of:

continuing if said off-Diagonal terms are not essentially zero (0.0); and if said off-Diagonal terms are essentially zero (0.0), first rotating the material system so that said Off-Diagonal terms become other than essentially zero (0.0).

25. A method of evaluating mathematical model parameters as in claim 14 wherein, after providing optically thick material system, a screening step of evaluating of components of a selection from the group consisting of:

a material system representing Jones Matrix; and a material system representing Mueller Matrix;

is practiced, followed by practicing a selection from the group consisting of:

continuing if said off-Diagonal terms are not essentially zero (0.0); and if said off-Diagonal terms are essentially zero (0.0), first rotating the material system so that said Off-Diagonal terms become other than essentially zero (0.0).

26. A method of evaluating mathematical model parameters as in claim 19 wherein, after providing optically thick material system, a screening step of evaluating of components of a selection from the group consisting of:

a material system representing Jones Matrix; and a material system representing Mueller Matrix;

is practiced, followed by practicing a selection from the group consisting of:

continuing if said off-Diagonal terms are not essentially zero (0.0); and if said off-Diagonal terms are essentially zero (0.0), first rotating the material system so that said Off-Diagonal terms become other than essentially zero (0.0).

27. A method of evaluating mathematical model parameters as in claim 21 wherein, after providing optically thick material system, a screening step of evaluating of components of a selection from the group consisting of:

a material system representing Jones Matrix; and a material system representing Mueller Matrix;

is practiced, followed by practicing a selection from the group consisting of:

continuing if said off-Diagonal terms are not essentially zero (0.0); and if said off-Diagonal terms are essentially zero (0.0), first rotating the material system so that said Off-Diagonal terms become other than essentially zero (0.0).

* * * * *